(12) United States Patent
Ikeda et al.

(10) Patent No.: US 10,994,011 B2
(45) Date of Patent: May 4, 2021

(54) PHARMACEUTICAL COMPOSITION COMPRISING ANTI-HUMAN TSLP RECEPTOR ANTIBODY

(71) Applicant: ASTELLAS PHARMA INC., Chuo-ku (JP)

(72) Inventors: Megumi Ikeda, Chuo-ku (JP); Akinori Chikushi, Chuo-ku (JP)

(73) Assignee: ASTELLAS PHARMA INC., Chuo-ku (JP)

( * ) Notice: Subject to any disclaimer, the term of this patent is extended or adjusted under 35 U.S.C. 154(b) by 127 days.

(21) Appl. No.: 16/063,124

(22) PCT Filed: Dec. 16, 2016

(86) PCT No.: PCT/JP2016/087480
§ 371 (c)(1),
(2) Date: Jun. 15, 2018

(87) PCT Pub. No.: WO2017/104778
PCT Pub. Date: Jun. 22, 2017

(65) Prior Publication Data
US 2019/0111129 A1    Apr. 18, 2019

(30) Foreign Application Priority Data
Dec. 18, 2015 (JP) .............................. JP2015-246826

(51) Int. Cl.
| | | |
|---|---|---|
| A61K 39/395 | (2006.01) | |
| A61K 47/12 | (2006.01) | |
| A61K 9/00 | (2006.01) | |
| A61K 9/08 | (2006.01) | |
| A61K 47/02 | (2006.01) | |
| A61K 47/18 | (2017.01) | |
| C07K 16/28 | (2006.01) | |
| A61K 9/19 | (2006.01) | |
| C07K 16/24 | (2006.01) | |
| A61K 47/10 | (2017.01) | |
| A61K 47/26 | (2006.01) | |

(52) U.S. Cl.
CPC ...... *A61K 39/39591* (2013.01); *A61K 9/0019* (2013.01); *A61K 9/08* (2013.01); *A61K 47/02* (2013.01); *A61K 47/10* (2013.01); *A61K 47/12* (2013.01); *A61K 47/183* (2013.01); *A61K 47/26* (2013.01); *C07K 16/24* (2013.01); *C07K 16/2866* (2013.01); *A61K 9/19* (2013.01); *C07K 2317/21* (2013.01)

(58) Field of Classification Search
CPC ............ A61K 39/39591; A61K 47/183; A61K 47/02; A61K 9/19; A61K 2039/505; C07K 16/2866
See application file for complete search history.

(56) References Cited

U.S. PATENT DOCUMENTS

| | | |
|---|---|---|
| 8,758,747 B2 | 6/2014 | Kallmeyer et al. |
| 2003/0180287 A1 | 9/2003 | Gombotz et al. |
| 2007/0172475 A1 | 7/2007 | Matheus et al. |
| 2007/0243185 A1 | 10/2007 | Gombotz et al. |
| 2008/0286280 A1 | 11/2008 | Kallmeyer et al. |
| 2010/0086559 A1 | 4/2010 | Gombotz et al. |
| 2010/0285011 A1 | 11/2010 | Morichika et al. |
| 2012/0148587 A1 | 6/2012 | Gombotz et al. |
| 2013/0344088 A1 | 12/2013 | Cosenza et al. |
| 2014/0248274 A1 | 9/2014 | Kallmeyer et al. |
| 2014/0377264 A1 | 12/2014 | Gombotz et al. |
| 2016/0046720 A1 | 2/2016 | Sato et al. |
| 2017/0051039 A1 | 2/2017 | Gombotz et al. |
| 2019/0144523 A1 | 5/2019 | Gombotz et al. |

FOREIGN PATENT DOCUMENTS

| | | |
|---|---|---|
| JP | 2007-522157 A | 8/2007 |
| JP | 2015-521593 A | 7/2015 |
| RU | 2 390 353 C2 | 3/2008 |
| RU | 2 497 544 C2 | 2/2012 |
| WO | WO 03/072060 A2 | 9/2003 |
| WO | WO 2004/091658 A1 | 10/2004 |
| WO | WO 2009/084659 A1 | 7/2009 |
| WO | WO 2010/106812 A1 | 9/2010 |
| WO | WO 2012/151199 A1 | 11/2012 |
| WO | WO 2013/186700 A1 | 12/2013 |
| WO | WO 2014/031718 A1 | 2/2014 |
| WO | WO 2014/143909 A1 | 9/2014 |
| WO | WO 2015/020193 A1 | 2/2015 |

OTHER PUBLICATIONS

Search Report and Written Opinion dated Feb. 11, 2019 in corresponding Singaporean Patent Application No. 11201805123X, 9 pages.
Written Opinion of the International Searching Authority dated Feb. 21, 2017 in PCT/JP2016/087480 (English Translation only), 8 pages.
Extended European Search Report dated Aug. 23, 2019 in European Patent Application No. 16875754.0, 8 pages.
International Search Report dated Feb. 21, 2017, in PCT/JP2016/087480 filed Dec. 16, 2016.
Arakawa, T., "Role of Arginine in Development of Biopharmaceuticals", The Pharmaceutical Society of Japan, vol. 130, No. 6, 2010, pp. 793-800, with an English Abstract.

(Continued)

*Primary Examiner* — Ruixiang Li
(74) *Attorney, Agent, or Firm* — Oblon, McClelland, Maier & Neustadt, L.L.P.

(57) ABSTRACT

Provided is a stable pharmaceutical composition comprising an anti-human TSLP receptor antibody, capable of inhibiting the generation of chemically modified substances, such as deamidated forms and oxidized forms, or degradants, or multimers. The pharmaceutical composition comprises an anti-human TSLP receptor antibody, a pharmaceutically acceptable buffer, arginine or a pharmaceutically acceptable salt thereof, and a surfactant.

14 Claims, 3 Drawing Sheets
Specification includes a Sequence Listing.

(56) References Cited

OTHER PUBLICATIONS

Combined Russian Office Action and Search Report dated Mar. 10, 2020 in Russian Patent Application No. 2018126355 (with English translation), 24 pages.
Daugherty A.L. et al, Formulating and Delivery Issues for Monoclonal Antibody Therapeutics AdvDrug Deilv Rev, May 22, 2006, vol. 58, No. 5-6, pp. 686-706.
Singapore Office Action dated Jun. 16, 2020, in corresponding Singapore Application No. 11201805123X filed Dec. 16, 2016.
Office Action dated Oct. 23, 2020, in corresponding Indonesian Patent Application No. PID201805244 (with English translation).
Office Action dated Jan. 28, 2021, in Taiwan Application No. 105141843, filed Dec. 16, 2016 (with English Translation).

PHARMACEUTICAL COMPOSITION COMPRISING ANTI-HUMAN TSLP RECEPTOR ANTIBODY

TECHNICAL FIELD

The present invention relates to a stable pharmaceutical composition comprising an anti-human TSLP receptor antibody. Further, the present invention relates to a stable and highly concentrated pharmaceutical composition comprising an anti-human TSLP receptor antibody.

BACKGROUND ART

It is known that a monoclonal antibody that specifically binds to a human TSLP (thymic stromal lymphopoietin) receptor and inhibits the action of humans TSLP via the human TSLP receptor is useful for prevention and/or treatment of various diseases in which human TSLP and a human TSLP receptor are involved in disease pathology (for example, prevention and/or treatment of asthma) (Patent literature 1).

Patent literature 1 discloses fully human type T7-27 its an anti-human TSLP receptor antibody, and discloses that it inhibits the expression of TARC (thymus and activation-regulated chemokine) mRNA induced by TSLP and the production of MDC (macrophage-derived chemokine) protein, and that it suppresses an allergic reaction in a monkey ascaris antigen sensitization model.

On the other hand, various antibody medicines have been developed in recent years, and are actually provided for the medical field. Many antibody medicines are administered by intravenous administration, subcutaneous administration, or the like, and thus are provided as a form of a parenteral pharmaceutical composition, such as a liquid preparation, a lyophilized preparation, or the like, for the medical field. Since parenteral pharmaceutical compositions are presumed to be directly administered into the body, stable pharmaceutical preparations are required.

Also, from a pharmaceutical viewpoint, since intravenous administration or subcutaneous administration is assumed as the route of administration, in the case of making the same pharmaceutical preparation, taking into consideration the dose for subcutaneous administration, it is desirable that the pharmaceutical preparation is a high concentration preparation.

However, in a solution containing a high concentration of antibody, undesirable phenomena may occur, including the formation of insoluble aggregates and/or soluble aggregates. The insoluble aggregates and soluble aggregates are formed in a solution state by the association of antibody molecules. Further, when the solution is stored for a long period of time, deamidation of an asparagine residue may decrease the physiological activity of the antibody molecule.

As a technique concerning a highly concentrated antibody and a protein preparation, an invention relating to a stable, liquid preparation of low turbidity comprising a protein or antibody in an amount of 100 to 260 mg/mL, arginine hydrochloride in an amount of 50 to 200 mmol/L, histidine in an amount of 10 to 100 mmol/L polysorbate in an amount of 0.01 to 0.1%, wherein the preparation has a pH ranging from 5.5 to 7.0, a kinematic viscosity of about 50 cs or less, and osmolality ranging from 200 mOsm/kg to 450 mOsm/kg, is known (Patent literature 2). However, the anti-human TSLP receptor antibody is not disclosed nor suggested in Patent literature 2.

Patent literatures 3 discloses an invention relating to a stable pharmaceutical composition containing an anti-TSLP antibody, but it is not an invention relating to an anti-TSLP receptor antibody.

CITATION LIST

Patent Literature

[Patent Literature 1] WO 2015/020193
[Patent Literature 2] WO 2004/091658
[Patent literature 3] WO 2014/031718

SUMMARY OF INVENTION

Technical Problem

An object of the present invention is to provide a stable pharmaceutical composition comprising fully human type T7-27, which is an anti-human TSLP receptor antibody.

More particularly, an object of the present invention is to provide a pharmaceutical composition comprising fully human type T7-27, which is an anti-human TSLP receptor antibody, for example, (i) a pharmaceutical composition capable of suppressing the generation of chemically modified substances, such as deamidated forms and oxidized forms, or degradants or multimers, which increase due to heat, (ii) a pharmaceutical composition capable of suppressing the generation of oxidized forms, promoted by the addition of arginine, (iii) a pharmaceutical composition capable of suppressing the generation of microparticles, which increase after physical stress, or (iv) a pharmaceutical composition capable of suppressing the generation of oxidized forms, which increase when the concentrations of a surfactant is high.

Solution to Problem

The present inventors found that a stable pharmaceutical composition could be prepared by formulating fully human type T7-27, which was an anti-human TSLP receptor antibody, in an arginine solution (Example 2 below), that a stable pharmaceutical composition could be prepared by adjusting the pH of the solution to an appropriate range, or using various buffer components (Examples 1, 3, and 4 below), and a further stable pharmaceutical composition could be prepared by using a surfactant, adjusting the antibody concentration, or the like, and completed the present invention.

The present invention relates to:

[1] a stable pharmaceutical composition comprising an anti-human TSLP receptor antibody, a pharmaceutically acceptable buffer, arginine or a pharmaceutically acceptable salt thereof, and a surfactant, wherein the following (1) and or (2) is contained as the anti-human TSLP receptor antibody;

(1) an anti-human TSLP receptor antibody comprising a heavy chain consisting of the amino acid sequence of SEQ ID NO: 1, and a light chain consisting of the amino acid sequence of SEQ ID NO: 3, and (2) an anti-human TSLP receptor antibody consisting of amino acid sequences of an antibody generated by a post-translational modification of the anti-human TSLP receptor antibody of (1);

[2] the pharmaceutical composition of [1], wherein the pharmaceutically acceptable buffer is one, or two or more selected from the group consisting of phosphoric acid, citric acid, acetic acid, succinic acid, histidine, ascorbic acid, glutamic acid, lactic acid, maleic acid, trometamol, and gluconic acid;

[3] the pharmaceutical composition of [1] or [2], wherein the pharmaceutically acceptable buffer is phosphoric acid;

[4] the pharmaceutical composition of any one of [1] or [3], wherein the concentration of the pharmaceutically acceptable buffer is 5 to 100 mmol/L;

[5] the pharmaceutical composition of any one of [1] or [4], wherein the pharmaceutical composition is a liquid preparation, or a lyophilized preparation or a spray-dried preparation;

[6] the pharmaceutical composition of [5], wherein the pharmaceutical composition is a liquid preparation;

[7] the pharmaceutical composition of [5], wherein when the pharmaceutical composition is a liquid preparation, a pH of the liquid preparation is 5 to 6, or when the pharmaceutical composition is a lyophilized preparation or a spray-dried preparation, a pH of a solution after reconstituting the preparation in water is 5 to 6;

[8] the pharmaceutical composition of [7], wherein the pharmaceutical composition is a liquid preparation, and the pH of the liquid preparation is 5 to 6;

[9] the pharmaceutical composition of any one of [1] to [8], wherein the concentration of the arginine or a pharmaceutically acceptable salt thereof is 700 mmol/L or less;

[10] the pharmaceutical composition of any one of [1] to [9], wherein the surfactant is one, or two or more selected from the group consisting of polysorbates and poloxamer 188;

[11] the pharmaceutical composition of any one of [1] to [10], wherein the surfactant is polysorbate 80;

[12] the pharmaceutical composition of any one of [1] to [11], wherein a content of the surfactant is 0.001 to 1% (w/v);

[13] the pharmaceutical composition of any one of [1] to [12], wherein the content of the surfactant is 0.01 to 0.2% (w/v);

[14] the pharmaceutical composition of any one of [5] to [13], wherein when the pharmaceutical composition is a liquid preparation, a content of the anti-human TSLP receptor antibody is 0.007 to 2 mmol/L, or when the pharmaceutical composition is a lyophilized preparation or a spray-dried preparation, a content of a solution after reconstituting the preparation in water is 0.007 to 2 mmol/L;

[15] the pharmaceutical composition of any one of [1] to [14], when the pharmaceutical composition is stored, each content of a degradant and a multimer is 10% or less, or a content of a chemically modified substance is 50% or less;

[16] the pharmaceutical composition of [1], comprising an anti-human TSLP receptor antibody comprising a heavy chain consisting of the amino acid sequence of SEQ ID NO: 1, and a light chain consisting of the amino acid sequence of SEQ ID NO: 3;

[17] the pharmaceutical composition of [1], comprising an anti-human TSLP receptor antibody consisting of amino acid sequences of an antibody generated by a post-translational modification of an anti-human TSLP receptor antibody comprising a heavy chain consisting of the amino acid sequence of SEQ ID NO: 1, and a light chain consisting of the amino acid sequence of SEQ ID NO: 3;

[18] the pharmaceutical composition of [1], comprising an anti-human TSLP receptor antibody comprising a heavy chain consisting of the amino acid sequence of amino acids 1-447 of SEQ ID NO: 1, and a light chain consisting of the amino acid sequence of SEQ ID NO: 3; and

[19] the pharmaceutical composition of [1], comprising an anti-human TSLP receptor antibody comprising a heavy chain consisting of the amino acid sequence of SEQ ID NO: 1, and a light chain consisting of the amino acid sequence of SEQ ID NO: 3, and an anti-human TSLP receptor antibody comprising a heavy chain consisting of the amino acid sequence of amino acids 1-447 of SEQ ID NO: 1, and a light chain consisting of the amino acid sequence of SEQ ID NO: 3.

Advantageous Effects of Invention

According to the present invention, a stable pharmaceutical composition comprising fully human type T7-27, which is an anti-human TSLP receptor antibody, more particularly, a stable pharmaceutical composition comprising an anti-human TSLP receptor antibody, capable of suppressing the generation of chemically modified substances, such as deamidated forms and oxidized forms, or degradants or multimers, or the generation of microparticles, can be provided.

BRIEF DESCRIPTION OF THE DRAWINGS

FIG. 1-2 shows the evaluation results of SEC and IEC obtained in Example 1 (SEC degradants).

FIG. 1-3 shows the evaluation results of SEC and IEC obtained in Example 1 (IEC main peak).

FIG. 2 shows the evaluation results of SEC obtained in Example 2.

FIG. 3-1 shows the results of arginine and pH in the group of phosphoric acid-containing formulations obtained in Example 3.

FIG. 3-2 shows the results of arginine and pH in the group of histidine-containing formulations obtained in Example 3.

FIG. 4-1 shows the evaluation results of HIC obtained in Example 5.

FIG. 4-2 shows the evaluation results of HIC obtained in Example 5.

DESCRIPTION OF EMBODIMENTS

Figure 1:
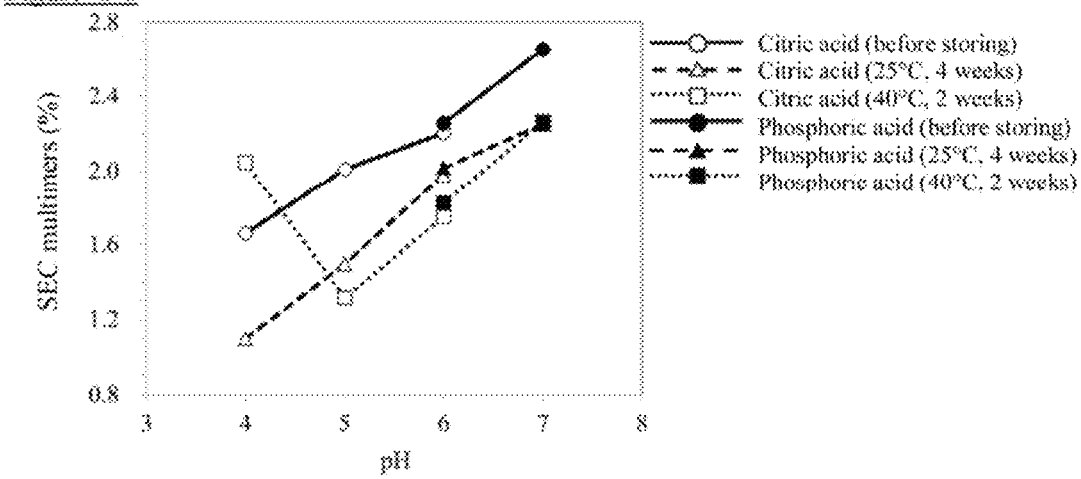
FIG. 1-1 shows the evaluation results of SEC and IEC obtained in Example 1 (SEC multimers).

The term "stable" as used herein means to have stability against, for example, heat, light, temperature, and/or humidity. For example, after a pharmaceutical composition is allowed to stand under predetermined conditions, it means that impurities contained in the pharmaceutical composition, for example, chemically modified substances, such as deamidated forms and oxidized forms, or degradants or multimers, are a specific amount or less. The amount are defined as percentage (%), by measuring the area of multimer peaks or degradant peaks detected by SEC by an automatic analysis method and dividing it by the sum of all peak areas including the main peak, by measuring the area of the main peak detected by IEC by an automatic analysis method and dividing it by the sum of all peak areas other than the main peak, or by measuring the area of a hydrophilic peak detected by HIC by an automatic integration method and dividing it by the sum of all peak areas including the main peak. The main peak as used herein means the peak of the active body.

The chemically modified substance is a structure generated by a chemical modification of part of the sequence of the antibody molecule. The amount of the chemically modified substances is defined as 0% to 70% as one embodiment, and 0% to 50% as another embodiment.

The deamidated form is a chemically modified substance in which a portion of the amino residues of the antibody molecule undergo a deamidation reaction. A measuring method of the deamidated form is not particularly limited, so long as the deamidated form can be measured. The measuring method includes, for example, ion exchange chromatography and the like. The amount of the deamidated forms is defined as 0% to 70% as one embodiment, 0% to 50% as another embodiment, and 0% to 30% as still another embodiment.

The oxidized form is a chemically modified substance in which part of the sequence of the antibody molecule is oxidized. A measuring method of the oxidized form is not particularly limited, so long as the oxidized form can be measured. The measuring method includes, for example, hydrophobic interaction chromatography, ion exchange chromatography, and the like. The amount of the oxidized forms is defined as 0% to 70% as one embodiment, and 0% to 50% another embodiment.

The degradant is a fragment generated by elimination of part of the antibody molecule. A measuring method of the degradant is not particularly limited, so long as the degradant can be measured. The measuring method includes, for example, size exclusion chromatography, gel electrophoresis, capillary electrophoresis, dynamic light scattering, light obscuration particle counting, micro flow imaging, and the like. The amount of the degradants is defined as 0% to 10% as one embodiment, and 0% to 5% as another embodiment.

The multimer is a complex produced by collecting a plurality of antibody molecules. A measuring method of the multimer is not particularly limited, so long as the multimer can be measured. The measuring method includes, for example size exclusion chromatography, gel electrophoresis, capillary electrophoresis, dynamic light scattering, light obscuration particle counting, micro flow imaging, and the like. The amount of the multimers is defined as 0% to 10% as one embodiment, and 0% to 5% as another embodiment.

The term "stable" as used herein means that the amount of the impurities is suppressed at least for 6 months, preferably for 1 year, more preferably for 2 years at refrigerating temperature (2° C. to 8° C.); at least for 3 months, preferably for 6 months, more preferably for 1 year at room temperature (22° C. to 28° C.), or at least 1 week, preferably for 2 weeks at 40° C. For example, the amount of the multimers and the amount of the degradants after storage at 5° C. for 2 years are each 10% or less, preferably 5% or less, more preferably 3% or less; the amount of the multimers and the amount of the degradants after storage at 25° C. for 3 months are each 10% or less, preferably 5% or less, more preferably 3% or less; or the amount of the multimers and the amount of the degradants after storage at 40° C. for 1 week are each 5% or less, preferably 3% or less.

The term "about" as used herein means, when it is used in connection with numerical variables, a larger variable value, in general, within an experimental error (for example, within the 95% confidence interval for the mean), or within ±10% of the indicated value, and all the values of the variable. In this connection, even in the case of a numerical value without "about", this interpretation shall be made.

There are five classes of antibodies IgG, IgM, IgA, IgD, and IgE. The basic structure of an antibody molecule is common to each class and is composed of a heavy chain having a molecular weight of 50,000 to 70,000 and a light chain of 20,000 to 30,000. The heavy chain usually consists of a polypeptide containing about 440 amino acids, and has a characteristic structure for each class, and the heavy chains of IgG, IgM, IgA, IgD, and IgE are called Igγ, Igμ, Igα, Igγ, and Igε, respectively. IgG further has subclasses IgG1, IgG2, IgG3, and IgG4, and the heavy chains thereof are called Igγ1, Igγ2, Igγ3, and Igγ4, respectively. The light chain usually consists of a polypeptide containing about 220 amino acids, and two types of light chains, L type and K type, are known, and called Igλ, and Igκ, respectively. With respect to the polypeptide constitution of the basic structure of an antibody molecule, two homologous heavy chains and two homologous light chains are linked by disulfide bonds (S—S bond) and noncovalent bonds, and the molecular weight is 150,000 to 190,000. Two types of light chains can pair with any heavy chain. An individual antibody molecule always consists of two identical light chains and two identical heavy chains.

There are four (five for the μ or ε chain) intrachain S—S bonds and two intrachain S—S bonds, and one loop is formed every 100 to 110 amino acid residues, and the steric structure is similar between each loop and is called a structural unit or a domain. The domain located at the amino terminus (N-terminus) for both heavy and light chains is not constant in its amino acid sequence, even if the antibody is a specimen that is the same class (subclass) from the same animal species, and a the domain is called a variable region, and each domain is called a heavy chain variable region and a light chain variable region. The amino acid sequence at the carboxy terminal (C-terminal) side from the variable region is almost constant for each class or subclass, and is called a constant region.

It is known that when an antibody is expressed in cells, the antibody undergoes a post-translational modification. As example of the post-translational modification in which an amino acid residue is changed, cleavage of lysine at the C-terminus of a heavy chain by carboxypeptidase, modification to pyroglutamic acid by pyroglutamylation of glutamine or glutamic acid at the N-terminus of heavy and light chains or the like, may be exemplified, and it is known that lysine at the C-terminus of a heavy chain is deleted, and modification to pyroglutamic acid occurs for most of the glutamine at the N-terminus of a heavy chain in various antibodies (Journal of Pharmaceutical Sciences 2008, Vol. 97, p. 2426). Further, it is known in the art that such a post-translational modification by pyroglutamylation at the N-terminus or lysine deletion at the C-terminus does not affect the antibody activity (Analytical Biochemistry, 2006, Vol. 348, p. 24-39).

As an anti-human TSLP receptor antibody, the pharmaceutical composition of the present invention comprises the anti-human TSLP receptor antibody of the following (1) and/or (2):

(1) an anti-human TSLP receptor antibody comprising a heavy chain consisting of the amino acid sequence of SEQ ID NO: 1, and a light chain consisting of the amino acid sequence of SEQ ID NO: 3, and (2) an anti-human TSLP receptor antibody consisting of amino acid sequences of an antibody generated by a post-translational modification of the anti-human TSLP receptor antibody comprising a heavy chain consisting of the amino acid sequence of SEQ ID NO: 1, and a light chain consisting of the amino acid sequence of SEQ ID NO: 3 (WO 2015/020193).

In an embodiment, the post-translational modification in the anti-human TSLP receptor antibody of (2) is pyroglutamylation at the N-terminus of a heavy chain variable region and/or lysine deletion at the C-terminus of a heavy chain for example as the anti-human TSLP receptor antibody of (2), an anti-human TSLP receptor antibody comprising a heavy chain consisting of the amino acid sequence of amino acids 1-447 of SEQ ID NO: 1, and a light chain consisting of the amino acid sequence of SEQ ID NO: 3 may be exemplified.

In an embodiment the pharmaceutical composition of the present invention comprises an anti-human TSLP receptor antibody comprising a heavy chain consisting of the amino acid sequence of SEQ ID NO: 1, and a light chain consisting of the amino acid sequence of SEQ ID NO: 3 and an anti-human TSLP receptor antibody comprising a heavy chain consisting of the amino acid sequence of amino acids 1-447 of SEQ ID NO: 1, and a light chain consisting of the amino acid sequence of SEQ ID NO: 3.

The anti-human TSLP receptor antibody used in the present invention can be easily prepared by those skilled in the art, based on the sequence information of the heavy chain and the light chain of the anti-human TSLP receptor antibody disclosed in the present specification, using methods known in the art. As a preparation method of the anti-human TSLP receptor antibody used in the present invention, a method disclosed in WO 2015/020193 may be exemplified.

The amount of the antibody in one unit pharmaceutical composition (preparation) is, for example, 0.001 mg to 1000 mg as one embodiment, and 0.01 mg to 100 mg as another embodiment. Each lower limit and each upper limit can be arbitrarily combined as desired.

When the pharmaceutical composition is in a solid state (for example, lyophilized preparation spray-dried preparation, or the like), the amount of the antibody is, for example, 0.001 mg to 1000 mg as one embodiment, and 0.01 mg to 100 mg as one embodiment. Each lower limit and each upper limit can be arbitrarily combined as desired.

The liquid volume when, dissolved at the time of use is, for example, 0.1 mL to 100 mL as an embodiment, and 1 mL to 10 mL as another embodiment. Each lower limit and each upper limit can be arbitrarily combined as desired.

When the pharmaceutical composition is a liquid state (liquid preparation), the concentration of the antibody is, for example, 1 mg/mL to 300 mg/mL (about 0.007 mmol/L to 2 mmol/L) as an embodiment, 1 mg/mL to 200 mg/mL (about 0.007 mmol/L to 1 mmol/L) as one embodiment, 1 mg/mL to 100 mg/mL (about 0.007 mmol/L to 0.7 mmol/L) as still another embodiment, and 10 mg/mL to 50 mg/mL (about 0.07 mmol/L to 0.3 mmol/L) as still another embodiment. Each lower limit and each upper limit can be arbitrarily combined as desired.

The dose is 0.001 mg to 1000 mg as one embodiment and 0.01 mg to 100 mg as another embodiment. Each lower limit and each upper limit can be arbitrarily combined as desired.

Indications include prevention and/or treatment of various diseases in which human TSLP and a human TSLP receptor are involved in disease pathology, for example, prevention and/or treatment of asthma.

A "pharmaceutically acceptable buffer" used in the present invention is not particularly limited, so long as it is pharmaceutically acceptable, and in a solution state, the pH of the solution can be adjusted within the desired pH range.

More particularly, the pH is, for example, 5 to 6 as one embodiment, and 5.0 to 6.0 as another embodiment. When the buffer is phosphoric acid or a salt thereof, the pH is preferably 5.5 to 5.7, and when the buffer is histidine or a salt thereof, the pH is preferably 5.3 to 6.0.

When the pharmaceutical composition is a liquid preparation, the pH is defined as the pH of the liquid preparation, and when the pharmaceutical composition is a lyophilized preparation or a spray-dried preparation, the pH is defined as the pH of a solution obtained by dissolving the preparation in water.

As the buffer component, for example, phosphoric acid (sodium or potassium), citric acid, acetic acid, succinic acid, histidine, ascorbic acid, glutamic acid, lactic acid, maleic acid, trometamol, gluconic acid, a pharmaceutically acceptable salt thereof, or the like, is included as one embodiment. Phosphoric acid, or a pharmaceutically acceptable salt thereof (sodium salt or potassium salt) is included as another embodiment. Sodium dihydrogenphosphate is included as still another embodiment.

One kind or two or more kinds of these buffer components can be appropriately used in appropriate amounts.

The concentration of the buffer is not particularly limited, so long as the pH can be adjusted within the desired pH range. More particularly, it is, for example, 5 to 100 mmol/L as an embodiment, 5 to 70 mmol/L as another embodiment, and 5 to 50 mmol/L as still another embodiment.

When the pharmaceutical composition is in a solution state (liquid preparation) dissolved with water for injection, the amount of the buffer is, for example, 0.1 to 100 mg/mL as an embodiment, and 0.1 to 50 mg/mL as another embodiment. When the pharmaceutical composition is in a solid state (lyophilized preparation or spray-dried preparation) by lyophilization or the like, for example, the amount after reconstitution with 1 mL of water for injection is 5 to 100 mmol/L as an embodiment, 5 to 70 mmol/L as another embodiment, and 5 to 50 mmol/L as still another embodiment.

"Arginine or a pharmaceutically acceptable salt thereof" used in the present invention is not particularly limited, so long as it is pharmaceutically acceptable arginine or a salt thereof. The arginine or a salt thereof has a function of stabilizing it. For example, L-arginine or L-arginine hydrochloride is included.

The amount of arginine or a pharmaceutically acceptable salt thereof is 150 mg/mL (about 700 mmol/L) or less (excluding no addition) as an embodiment, 100 mg/mL (about 500 mmol/L) or less (excluding no addition) as another embodiment, and 45 mg/mL (about 210 mmol/L) or less (excluding no addition). When the anti-human TSLP receptor antibody is 30 mg/mL (about 0.2 mmol/L) 30 mg/mL (about 140 mmol/L) is preferable in order to ensure isotonicity from the aspect of osmotic pressure. As the lower limit (excluding no addition), for example, 10 mg/mL (about 50 mmol/L) or more may be exemplified. Each lower limit and each upper limit can be arbitrarily combined as desired.

When the pharmaceutical composition is in a solution state (liquid preparation) dissolved with water for injection, for example, per 1 mL, the amount is 150 mg or lees (excluding no addition) as an embodiment, 100 mg or less (excluding no addition) as another embodiment, and 45 mg or less (excluding no addition) as still another embodiment, or when the pharmaceutical composition is in a solid state (lyophilized preparation) by lyophilization or the like, for example, after reconstitution with water for injection, the arginine concentration is 150 mg/ml (about 700 mmol/L) or less (excluding no addition) as an embodiment, 100 mg/mL (about 500 mmol/L) or less (excluding no addition) as another embodiment, and 45 mg/mL (about 210 mmol/L) or less (excluding no addition) as still another embodiment. When the anti-human TSLP receptor antibody is 30 mg/mL, about 140 mmol/L is preferable in order to ensure isotonicity from the aspect of osmotic pressure.

The surfactant used in the present invention is not particularly limited, so long as it is pharmaceutically acceptable and has surface activity.

More particularly, for example, nonionic surfactants (for example, sorbitan fatty acid esters, such as sorbitan monocaprylate, sorbitan monolaurate, sorbitan monopalmitate and the like; glycerin fatty acid esters, such as glycerol monocaprylate, glycerol monomyristate, glycerol monostearate, and the like, polyglycerol fatty acid esters, such as decaglyceryl monostearate, decaglyceryl distearate, decaglyceryl monolinoleate, and the like; polyoxyethylene sorbitan fatty acid esters, such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan trioleate, and the like; polyoxyethylene sorbitol fatty acid ester, such as polyoxyethylene sorbitol tetrastearate, polyoxyethylene sorbitol tetraoleate, and the like; polyoxyethylene glycerin fatty acid esters, such as polyoxyethylene glyceryl monostearate, and the like; polyethylene glycol fatty acid esters, such as polyethylene glycol distearate, and the like; polyoxyethylene alkyl ethers, such as polyoxyethylene lauryl ether, and the like, polyoxyethylene polyoxypropylene alkyl ethers, such as polyoxyethylene polyoxypropylene glycol ether, polyoxyethylene polyoxypropylene propyl ether, polyoxyethylene polyoxypropylene cetyl ether, and the like; polyoxyethylene alkylphenyl ethers, such as polyoxyethylene nonylphenyl ether, and the like; polyoxyethylene hydrogenated castor oil, such as polyoxyethylene castor oil, polyoxyethylene hydrogenated castor oil, and the like; polyoxyethylene beeswax derivatives, such as polyoxyethylene sorbitol beeswax, and the like; polyoxyethylene lanolin derivatives, such as polyoxyethylene lanolin, and the like; and surfactants having an HLB of 6 to 18, such as polyoxyethylene fatty acid amides, and the like (for example, polyoxyethylene octadecanamide, and the like)); anionic surfactants (for example, alkyl sulfates having a C10-C18 alkyl group, such as sodium cetyl sulfate, sodium lauryl sulfate, sodium oleyl sulfate, and the like; polyoxyethylene alkyl ether sulfate in which the average number of moles of added ethylene oxide units is 2 to 4 and the number of carbon atoms of the alkyl group is 10 to 18, such as sphingomyelin, polyoxyethylene lauryl sulfate, and the like; alkyl sulfosuccinate having C8-C18 alkyl group, such as sodium lauryl sulfosuccinate, and the like); natural surfactants, such as lecithin, glycerophospholipid, and the like; sphingophospholipids, such as sphingomyelin, and the like and sucrose esters of C12-C18 fatty acids, are included.

One kind or two or more kinds of these surfactants can be appropriately selected and used.

The surfactant is polyoxyethylene sorbitan fatty acid esters or polyoxyethylene polyoxypropylene alkyl ethers as an embodiment, polysorbates (for example, 20, 21, 40, 60, 65, 80, 81, or 85) or pluronic-type surfactants as another embodiment, polysorbates (for example, 20 or 80) or poloxamer 188 (pluronic F68) as still another embodiment, and is polysorbate 20 or polysorbate 80 as still another embodiment.

The amount of the surfactant is 0.001 to 1% (w/v) as an embodiment, 0.005 to 0.5% (w/v) as another embodiment, and 0.01 to 0.2% (w/v) as still another embodiment. Each lower limit and each upper limit can be arbitrarily combined as desired.

The pharmaceutical composition of the present invention can be provided as a parenteral pharmaceutical composition, such as a liquid preparation by filling a container with the solution, or a lyophilized preparation, a spray-dried preparation, or the like obtained by subjecting the solution to lyophilization or spray-drying. The preferred pharmaceutical composition is a liquid preparation.

To the pharmaceutical composition of the present invention, pharmaceutical additives, such as a suspending agent, a solubilizing agent, a tonicity agent, a preserving agent, an adsorption inhibitor, a diluting agent, a soothing agent, a sulfur-containing reducing agent, an antioxidant agent, or the like, can be appropriately added, if desired.

As the suspending agent for example, methyl cellulose, hydroxyethyl cellulose, gum arabic, tragacanth powder, sodium carboxymethyl cellulose, polyoxyethylene sorbitan monolaurate, and the like, may be exemplified.

As the solubilization agent, for example, polyoxyethylene hydrogenated castor oil, nicotinamide, polyoxyethylene sorbitan monolaurate, macrogol, castor oil fatty acid, ethyl ester, and the like, may be exemplified.

As the tonicity agent, for example sodium chloride, potassium chloride, calcium chloride, and the like, may be exemplified.

As the preserving agent, for example, methyl parahydroxybenzoate, ethyl parahydroxybenzoate, sorbic acid, phenol, cresol, chlorocresol, benzyl alcohol, and the like, may be exemplified.

As the adsorption inhibitor, for example, human serum albumin, lecithin, dextran, an ethylene oxide/propylene oxide copolymer, hydroxypropyl cellulose, methyl cellulose, polyoxyethylene hydrogenated castor oil, polyethylene glycol, and the like, may be exemplified.

As the diluting agent, for example, sodium citrate hydrate, xylitol, and the like, may be exemplified.

As the soothing agent, for example, inositol, lidocaine, and the like, may be exemplified.

As the sulfur-containing reducing agent, for example, N-acetyl cysteine, N-acetyl homocysteine, thioctic acid, thiodiglycol, thioethanolamine, thioglycerol, thiosorbitol, thioglycolic acid and a salt thereof, sodium thiosulfate, glutathione, a compound having a sulfhydryl group, such as a thioalkanoic acid having 1 to 7 carbon atoms, and the like, may be exemplified.

As the antioxidant agent, for example, erythorbic acid, dibutylhydroxytoluene, butylhydroxyanisole, α-tocopherol, tocopherol acetate, L-ascorbic acid and a salt thereof, L-ascorbyl palmitate, L-ascorbic acid stearate, sodium bisulfite, sodium sulfite, triamyl gallate, propyl gallate, or chelating agents, such as disodium ethylenediaminetetraacetate (EDTA), sodium pyrophosphate, sodium metaphosphate, and the like, may be exemplified.

These pharmaceutical additives can be used in an appropriate amount, within a range of art amount capable of achieving the desired effect of the present invention.

The method of producing the pharmaceutical composition of the present invention is characterized by comprising the anti-human TSLP receptor antibody, and arginine or a pharmaceutically acceptable salt thereof. Further, with respect to a composition containing other component, a method of producing a stable pharmaceutical composition by a known production method per se, comprising the anti-human TSLP receptor antibody, fully human type T7-27, is included.

The container, which is filled with the pharmaceutical composition of the present invention, may be selected in accordance with the purpose of use. The container includes ones having a form of a specified capacity, such as a vial, an ampoule, and a syringe, or ones with a large capacity, such as a bottle. The container includes a syringe (including a disposable syringe) as an embodiment. By filling the syringe with a solution in advance and providing it as a prefilled syringe solution preparation, an operation such as a dissolution operation or the like becomes unnecessary in the medical field, a prompt response is expected.

With respect to the material of the container, glass, plastics, or the like, may be exemplified. With respect to the surface treatment in the container, a silicone coating treatment, a sulfur treatment, a various low alkali treatment, and the like, may be earned out. By applying these treatments, it is expected to provide a more stable pharmaceutical composition.

EXAMPLES

The present invention will now be further illustrated by, but is by no means limited to, the following Comparative Examples, Examples, and Experimental Examples.

The anti-human TSLP receptor antibody used in the Comparative Examples, Examples, and Experimental Examples was prepared by the method described in WO 2015/020193 or a similar method, and the concrete preparation procedure is shown in the Referential Example.

The symbol "-" in Tables means "with no additive".

Referential Example: Preparation of Fully Human Type Anti-Human TSLP Receptor Antibody, Fully Human Type T7-27

With respect to fully human type T7-27 (hereinafter sometimes referred to as antibody A), which was a fully human type anti-human TSLP receptor antibody used in the Examples, the nucleotide sequence encoding the heavy chain is shown in SEQ ID NO: 2, the amino acid sequence encoded thereby is shown in SEQ ID NO: 1, the nucleotide sequence encoding the light chain is shown in SEQ ID NO: 4, and the amino acid sequence encoded thereby is shown in SEQ ID NO: 3.

In accordance with WO 2015/020193, a GS vector (Lonza) into which both genes for the heavy chain and the light chain of antibody A were inserted was constructed. CHOK1SV cells (Lonza) were transfected with the vector to obtain a stable expression strain of the antibody, and the antibody was expressed. The culture supernatant was purified by a protein A column (GE Healthcare Japan) and an ion exchange chromatography to obtain a purified antibody of the fully human type antibody. As a result of analyzing the amino acid modification of the purified antibody A, it was assumed that lysine deletion at the C-terminal of the heavy chain occurred in most of the purified antibody.

Example 1: Stabilization Effect by Selection of Optimum pH

For liquid preparations containing antibody A, the influence of pH on stabilization of the preparations was evaluated.

In this study, in order to evaluate the effect of pH, evaluation samples of sample Nos. A1 to A5 were prepared. The formulation of each evaluation sample is shown in Table 1-1 below.

TABLE 1-1

| Component | Function | A1 (/1 mL) | A2 (/1 mL) | A3 (/1 mL) | A4 (/1 mL) | A5 (/1 mL) |
|---|---|---|---|---|---|---|
| Antibody A | Active ingredient | 10 mg [approx. 0.07 mM] | 10 mg [approx. 0.07 mM] | 10 mg [approx. 0.07 mM] | 10 mg [approx. 0.07 mM] | 10 mg [approx. 0.07 mM] |
| Citric acid | Buffer | 3.84 mg [20 mM] | 3.84 mg [20 mM] | 3.84 mg [20 mM] | — | — |
| $Na_2HPO_4 \cdot 12H_2O$ | Buffer | — | — | — | 7.16 mg [20 mM] | 7.16 mg [20 mM] |
| L-Arginine•HCl | Stabilizer | 29.49 mg [140 mM] | 29.49 mg [140 mM] | 29.49 mg [140 mM] | 29.49 mg [140 mM] | 29.49 mg [140 mM] |
| Polysorbate 80 | Surfactant | 0.20 mg [0.15 mM] (0.02 w/v %) | 0.20 mg [0.15 mM] (0.02 w/v %) | 0.20 mg [0.15 mM] (0.02 w/v %) | 0.20 mg [0.15 mM] (0.02 w/v %) | 0.20 mg [0.15 mM] (0.02 w/v %) |
| HCl | pH adjustor | adjusted to pH 4.0 | adjusted to pH 5.0 | adjusted to pH 6.0 | adjusted to pH 6.0 | adjusted to pH 7.0 |
| NaOH | pH adjustor | | | | | |

In order to evaluate the stability of the liquid preparations, a thermal acceleration test (storage at 40° C. for 2 weeks and at 25° C. for 4 weeks) of each sample was performed. The quality of the antibody before and after the thermal acceleration was evaluated by size exclusion chromatography (SEC) and ion exchange chromatography (IEC). The analysis conditions are as follows.

Size Exclusion Chromatography (SEC)

A G3000 SWXL column for SEC (Tosoh) was connected to an HPLC system, and a mobile phase consisting of 10 mmol/L phosphoric acid and 500 mmol/L NaCl pH 6.8 was flowed at a flow rate of 0.5 mL/min. Each sample was injected in an amount of 50 µg in terms of protein (for example, 5.0 µL in the case of 10 mg/mL). The analysis time was 30 minutes, and the detection was carried out at UV 280 nm. The column temperature was set to 30° C., and the sample temperature was set to 5° C.

Ion Exchange Chromatography (IEC)

A Propac WCX 10 column for IEC (Dionex) was connected to an HPLC system. A mobile phase consisting of 20 mmol/L MES pH 6.0 was connected to a mobile phase A line, and a mobile phase consisting of 20 mmol/L MES and 500 mmol/L NaCl pH 6.0 was connected to a mobile phase B line, and the mobile phases were flowed at a flow rate of 1 mL/min. The samples were diluted to 1 mg/mL with the mobile phase A, and 10 µL was injected. The IEC gradient program of Table 1-2 was applied. The detection was carried out at UV 280 nm. The column temperature was set to 40° C., and the sample temperature was set to 5° C.

TABLE 1-2

| Time (min.) | Mobile phase B % |
|---|---|
| 0 | 15 |
| 5 | 15 |
| 55 | 30 |
| 55.1 | 100 |
| 65 | 100 |
| 65.1 | 15 |
| 80 | 15 |

The areas of multimer peaks and degradant peaks detected by SEC and the area of the main peak detected by IEC were measured by an automatic analysis method to determine the amounts (%) thereof. The amounts are defined as percentage (%), by measuring the area of multimer peaks or degradant peaks detected by SEC by an automatic analysis method and dividing it by the sum of all peak areas including the main peak, or by measuring the area of the main peak detected by IEC by an automatic analysis method and dividing it by the sum of all peak areas other than the main peak. The main peak as used herein means the peak of the active body.

Figures 1, 2:
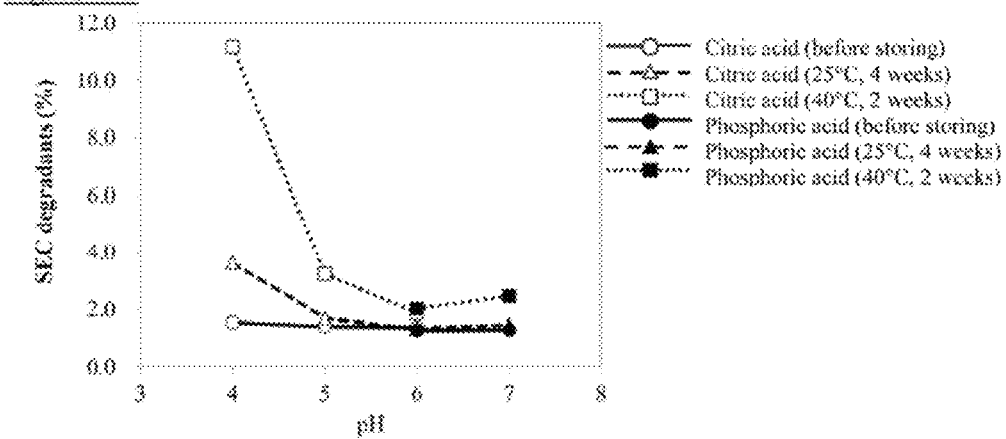
Figures 1, 2, 3:
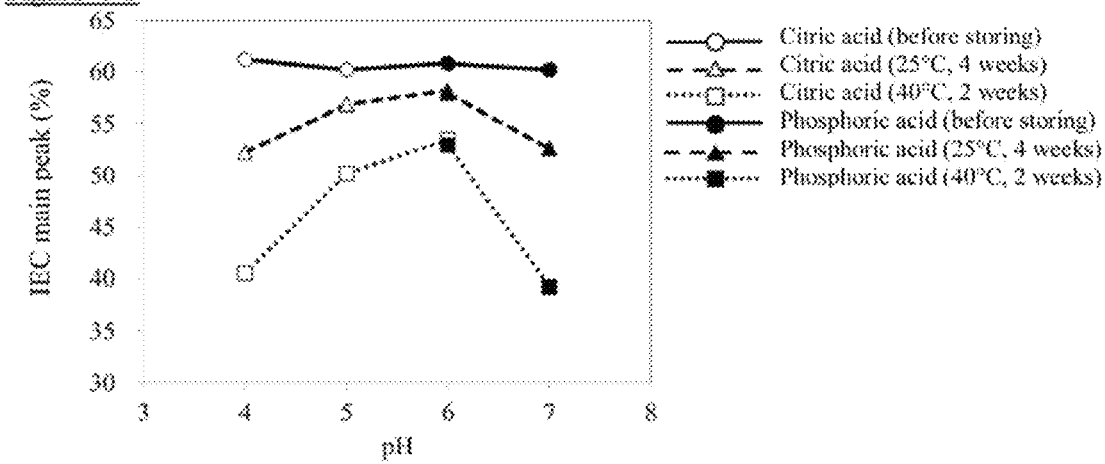
Figure 2:
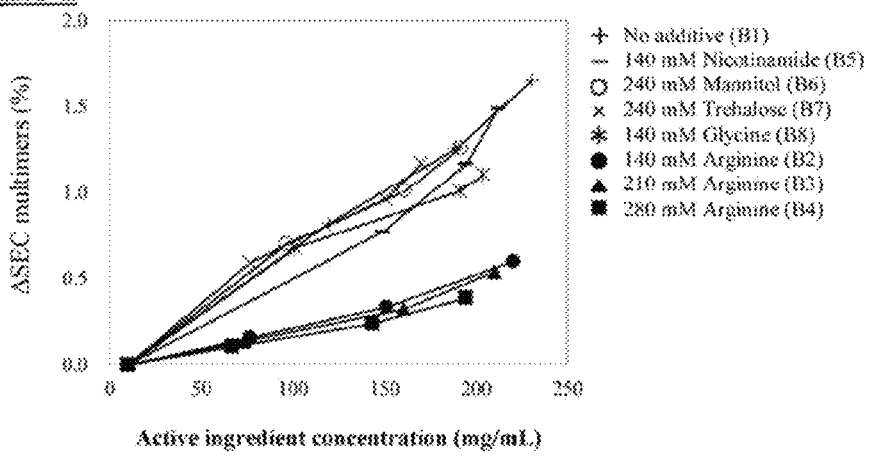
Figures 1, 3:
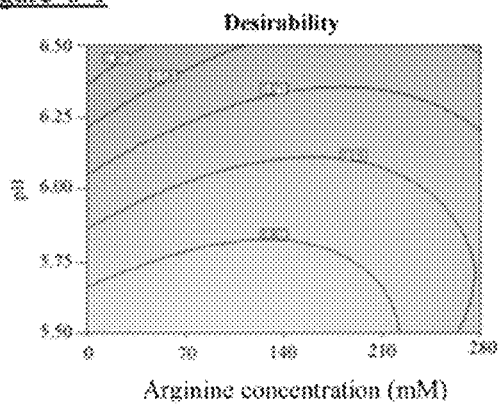
Figures 2, 3:
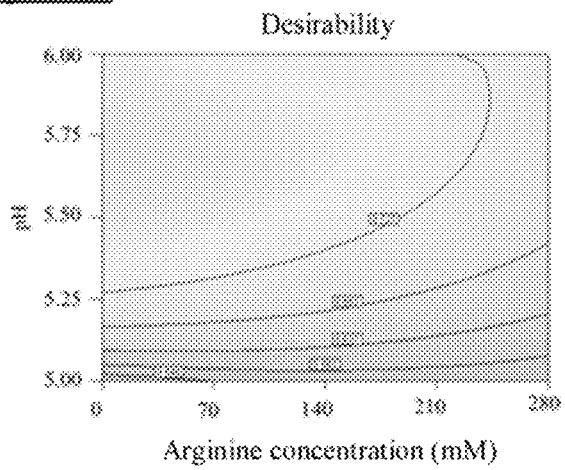

The evaluation results of SEC and IEC obtained in this Example are shown in FIGS. 1-1, 1-2, and 1-3. With respect to the SEC multimers, except for the storage at 40° C. for 2 weeks, the pH tended to increase them, particularly at a high pH (FIG. 1-1). On the other hand, with respect to the SEC degradants, the pH tended to increase them, particularly at a low pH (FIG. 1-2). With respect to the IEC main peak, the decrease was the smallest around pH 5-6, and it was the most stable (FIG. 1-3). The above results were comprehensively judged, and it was confirmed that the optimum pH was around pH 5-6.

Example 2: Suppression Effect of Arginine on Increased Multimers

For liquid preparations containing antibody A, the suppression effect of arginine on increased multimers was evaluated.

In this study, sample Nos. B1 to B4 with different amounts of arginine added were prepared. The formulate of each evaluation, sample is shown in Table 2-1 below.

TABLE 2-1

| Component | Function | B1 (/1 mL) | B2 (/1 mL) | B3 (/1 mL) | B4 (/1 mL) |
|---|---|---|---|---|---|
| Antibody A | Active ingredient | 10 mg [approx. 0.07 mM] | 10 mg [approx. 0.07 mM] | 10 mg [approx. 0.07 mM] | 10 mg [approx. 0.07 mM] |
| L-Histidine | Buffer | 3.10 mg [20 mM] | 3.10 mg [20 mM] | 3.10 mg [20 mM] | 3.10 mg [20 mM] |
| L-Arginine•HCl | Stabilizer | — | 29.49 mg [140 mM] | 44.24 mg [210 mM] | 58.98 mg [280 mM] |
| HCl | pH adjustor | adjusted to pH 6.0 | adjusted to pH 6.0 | adjusted to pH 6.0 | adjusted to pH 6.0 |
| NaOH | pH adjustor | | | | |

Each prepared sample listed in Table 2-1 was concentrated using spin columns to prepare samples B1-2 to B1-4, B2-2 to B2-4, B3-2 to B3-4, and B4-2 to B4-4. The formulation of each sample is shown in Table 2-2 below.

TABLE 2-2

| Component | Function | B1-2 (/1 mL) | B2-2 (/1 mL) | B3-2 (/1 mL) | B4-2 (/1 mL) |
|---|---|---|---|---|---|
| Antibody A | Active ingredient | 120 mg [approx. 0.8 mM] | 77 mg [approx. 0.5 mM] | 74 mg [approx. 0.5 mM] | 67 mg [approx. 0.4 mM] |
| L-Histidine | Buffer | 3.10 mg [20 mM] | 3.10 mg [20 mM] | 3.10 mg [20 mM] | 3.10 mg [20 mM] |
| L-Arginine•HCl | Stabilizer | — | 29.49 mg [140 mM] | 44.24 mg [210 mM] | 58.98 mg [280 mM] |

| Component | Function | B1-3 (/1 mL) | B2-3 (/1 mL) | B3-3 (/1 mL) | B4-3 (/1 mL) |
|---|---|---|---|---|---|
| Antibody A | Active ingredient | 189 mg [approx. 1.3 mM] | 151 mg [approx. 1.0 mM] | 161 mg [approx. 1.1 mM] | 144 mg [approx. 1.0 mM] |
| L-Histidine | Buffer | 3.10 mg [20 mM] | 3.10 mg [20 mM] | 3.10 mg [20 mM] | 3.10 mg [20 mM] |
| L-Arginine•HCl | Stabilizer | — | 29.49 mg [140 mM] | 44.24 mg [210 mM] | 58.98 mg [280 mM] |

| Component | Function | B1-4 (/1 mL) | B2-4 (/1 mL) | B3-4 (/1 mL) | B4-4 (/1 mL) |
|---|---|---|---|---|---|
| Antibody A | Active ingredient | 231 mg [approx. 1.5 mM] | 221 mg [approx. 1.5 mM] | 210 mg [approx. 1.4 mM] | 195 mg [approx. 1.3 mM] |
| L-Histidine | Buffer | 3.10 mg [20 mM] | 3.10 mg [20 mM] | 3.10 mg [20 mM] | 3.10 mg [20 mM] |
| L-Arginine•HCl | Stabilizer | — | 29.49 mg [140 mM] | 44.24 mg [210 mM] | 58.98 mg [280 mM] |

Comparative Example 1

Sample Nos. B5 to B8 containing nicotinamide, mannitol, trehalose, or glycine were prepared. The formulation of each evaluation sample is shown in Table 2-3 below.

TABLE 2-3

| Component | Function | B5 (/1 mL) | B6 (/1 mL) | B7 (/1 mL) | B8 (/1 mL) |
|---|---|---|---|---|---|
| Antibody A | Active ingredient | 10 mg [approx. 0.07 mM] | 10 mg [approx. 0.07 mM] | 10 mg [approx. 0.07 mM] | 10 mg [approx. 0.07 mM] |
| L-Histidine | Buffer | 3.10 mg [20 mM] | 3.10 mg [20 mM] | 3.10 mg [20 mM] | 3.10 mg [20 mM] |
| Nicotinamide | Stabilizer | 17.10 mg [140 mM] | — | — | — |
| Mannitol | Stabilizer | — | 43.72 mg [240 mM] | — | — |
| Trehalose (2H$_2$O) | Stabilizer | — | — | 90.80 mg [240 mM] | — |
| Glycine | Stabilizer | — | — | — | 10.51 mg [140 mM] |
| HCl | pH adjustor | adjusted to pH 6.0 | adjusted to pH 6.0 | adjusted to pH 6.0 | adjusted to pH 6.0 |
| NaOH | pH adjustor | | | | |

Each prepared sample listed in Table 2-3 was concentrated using spin columns to prepare samples B5-2 to B5-4, B6-2 to B6-4, B7-2 to B7-4, and B8-2 to B8-4. The formulation of each sample is shown in Table 2-4 below.

TABLE 2-4

| Component | Function | B5-2 (/1 mL) | B6-2 (/1 mL) | B7-2 (/1 mL) | B8-2 (/1 mL) |
|---|---|---|---|---|---|
| Antibody A | Active ingredient | 149 mg [approx. 1.0 mM] | 97 mg [approx. 0.6 mM] | 77 mg [approx. 0.5 mM] | 101 mg [approx. 0.7 mM] |
| L-Histidine | Buffer | 3.10 mg [20 mM] | 3.10 mg [20 mM] | 3.10 mg [20 mM] | 3.10 mg [20 mM] |
| Nicotinamide | Stabilizer | 17.10 mg [140 mM] | — | — | — |
| Mannitol | Stabilizer | — | 43.72 mg [240 mM] | — | — |
| Trehalose (2H$_2$O) | Stabilizer | — | — | 90.80 mg [240 mM] | — |
| Glycine | Stabilizer | — | — | — | 10.51 mg [140 mM] |

| Component | Function | B5-3 (/1 mL) | B6-3 (/1 mL) | B7-3 (/1 mL) | B8-3 (/1 mL) |
|---|---|---|---|---|---|
| Antibody A | Active ingredient | 195 mg [approx. 1.3 mM] | 161 mg [approx. 1.1 mM] | 151 mg [approx. 1.0 mM] | 191 mg [approx. 1.3 mM] |
| L-Histidine | Buffer | 3.10 mg [20 mM] | 3.10 mg [20 mM] | 3.10 mg [20 mM] | 3.10 mg [20 mM] |
| Nicotinamide | Stabilizer | 17.10 mg [140 mM] | — | — | — |
| Mannitol | Stabilizer | — | 43.72 mg [240 mM] | — | — |
| Trehalose (2H$_2$O) | Stabilizer | — | — | 90.80 mg [240 mM] | — |
| Glycine | Stabilizer | — | — | — | 10.51 mg [140 mM] |

| Component | Function | B5-4 (/1 mL) | B6-4 (/1 mL) | B7-4 (/1 mL) | B8-4 (/1 mL) |
|---|---|---|---|---|---|
| Antibody A | Active ingredient | 212 mg [approx. 1.4 mM] | 192 mg [approx. 1.3 mM] | 170 mg [approx. 1.1 mM] | 204 mg [approx. 1.4 mM] |
| L-Histidine | Buffer | 3.10 mg [20 mM] | 3.10 mg [20 mM] | 3.10 mg [20 mM] | 3.10 mg [20 mM] |
| Nicotinamide | Stabilizer | 17.10 mg [140 mM] | — | — | — |
| Mannitol | Stabilizer | — | 43.72 mg [240 mM] | — | — |
| Trehalose (2H$_2$O) | Stabilizer | — | — | 90.80 mg [240 mM] | — |
| Glycine | Stabilizer | — | — | — | 10.51 mg [140 mM] |

Each of these samples was evaluated by size exclusion chromatography (SEC). The analysis conditions are as follows.

Size Exclusion Chromatography (SEC)

A G3000 SWXL column for SEC (Tosoh) was connected to an HPLC system, and a mobile phase consisting of 10 mmol/L phosphoric acid and 500 mmol/L NaCl pH 6.8 was flowed at a flow rate of 0.5 mL/min. Each sample was injected in an amount of 100 μg in terms of protein for the study of concentration. The analysis time was 30 minutes, and the detection was carried out at UV 280 nm. The column temperature as set to 30° C., and the sample temperature was set to 20° C.

The area of multimer peaks detected by SEC was measured by an automatic analysis method to determine the amount (%) thereof. The amount is defined as percentage (%) by measuring the area of multimer peaks detected by SEC, and dividing it by the sum of all peak areas including the main peak. The main peak as used herein means the peak of the active body.

The evaluation result (increase of multimer peaks %) of SEC obtained in this Example and Comparative Example are shown in FIG. 2. In the preparations containing arginine (B2, B2-2 to B2-4, B5, B3-2 to B3-4, B4, and B4-2 to B4-4), an increase in multimers accompanying the increase in the concentration of the active ingredient was remarkably suppressed. On the other hand, in the preparations without arginine (B1, and B1-2 to B1-4) and the preparations with nicotinamide, mannitol, trehalose, or glycine (B5, B5-2 to B5-4, B6, B6-2 to B6-4, B7, B7-2 to B7-4, B8, and B8-2 to B8-4), an increase in multimers accompanying the increase in the concentration of the active ingredient was not suppressed, it was possible to confirm the suppression effect of arginine on increased multimers when the concentration of the active ingredient was increased.

The difference in arginine concentration did not affect the suppression effect on increased multimers (B2, B2-2 to B2-4, B3, B3-2 to B3-4, B4, and B4-2 to B4-4).

Example 3: Promoting Effect of Arginine, Histidine, and pH on Increased HIC Hydrophilic Peak For liquid preparations containing antibody A, the influence of arginine, histidine, and pH on an increased HIC hydrophilic peak was evaluated.

In this study, in order to evaluate the influence of arginine, histidine, and pH, evaluation samples of sample Nos. C1 to C9 were prepared. The formulation of each evaluation sample is shown in Table 3-1 below.

TABLE 3-1

| Component | Function | C1 (/1 mL) | C2 (/1 mL) | C3 (/1 mL) | C4 (/1 mL) | C5 (/1 mL) |
|---|---|---|---|---|---|---|
| Antibody A | Active ingredient | 10 mg [approx. 0.07 mM] | 10 mg [approx. 0.07 mM] | 10 mg [approx. 0.07 mM] | 10 mg [approx. 0.07 mM] | 10 mg [approx. 0.07 mM] |
| Na$_2$HPO$_4$·12H$_2$O | Buffer | — | — | 7.16 mg [20 mM] | 7.16 mg [20 mM] | 7.16 mg [20 mM] |
| L-Histidine | Buffer | 3.10 mg [20 mM] | 3.10 mg [20 mM] | — | — | — |
| Citric acid | Buffer | — | — | — | — | — |
| L-Arginine·HCl | Stabilizer | — | 29.49 mg [140 mM] | — | 29.49 mg [140 mM] | — |
| Sorbitol | Stabilizer | — | — | — | — | — |
| Polysorbate 80 | Surfactant | — | 0.20 mg [0.15 mM] (0.02 w/v %) | — | 0.20 mg [0.15 mM] (0.02 w/v %) | — |

TABLE 3-1-continued

| HCl<br>NaOH | pH adjustor<br>pH adjustor | adjusted to<br>pH 6.0 | adjusted to<br>pH 6.0 | adjusted to<br>pH 6.0 | adjusted to<br>pH 6.0 | adjusted to<br>pH 7.0 |
|---|---|---|---|---|---|---|
| Component | Function | C6 (/1 mL) | C7 (/1 mL) | C8 (/1 mL) | C9 (/1 mL) | |
| Antibody A | Active ingredient | 10 mg [approx. 0.07 mM] | 10 mg [approx. 0.07 mM] | 10 mg [approx. 0.07 mM] | 10 mg [approx. 0.07 mM] | |
| Na$_2$HPO$_4$•12H$_2$O | Buffer | 7.16 mg [20 mM] | — | — | 7.16 mg [20 mM] | |
| L-Histidine | Buffer | — | — | — | — | |
| Citric acid | Buffer | — | 3.84 mg [20 mM] | 3.84 mg [20 mM] | — | |
| L-Arginine•HCl | Stabilizer | 29.49 mg [140 mM] | 29.49 mg [140 mM] | — | — | |
| Sorbitol | Stabilizer | — | — | 43.72 mg [240 mM] | 43.72 mg [240 mM] | |
| Polysorbate 80 | Surfactant | 0.20 mg [0.15 mM] (0.02 w/v %) | 0.20 mg [0.15 mM] (0.02 w/v %) | 0.20 mg [0.15 mM] (0.02 w/v %) | 0.20 mg [0.15 mM] (0.02 w/v %) | |
| HCl<br>NaOH | pH adjustor<br>pH adjustor | adjusted to<br>pH 7.0 | adjusted to<br>pH 6.0 | adjusted to<br>pH 6.0 | adjusted to<br>pH 6.0 | |

In order to evaluate the stability of the liquid preparations, a storage stability test (storage at 5° C. for 5 months) of each sample was performed. The quality of the antibody after the storage was evaluated by hydrophobic interaction chromatography (HIC). The analysts conditions are as follows.

Hydrophobic Interaction Chromatography (HIC)

Two ProPac HIC-10 columns, for HIC (Dionex) were connected to an HPLC system. A mobile phase consisting of 800 mmol/L ammonium sulfate, 20 mmol/L sodium phosphate pH7.0 was connected to a mobile phase A line, and a mobile phase consisting of 20 mmol/L sodium phosphate pH7.0 was connected to a mobile phase B line, and the mobile phases were flowed at a flow rate of 0.8 mL/min. The samples were diluted to 1 mg/mL with the mobile phase A, and 50 μL was injected. The HIC gradient program of Table 3-2 was applied. The detection was carried out at UV 280 nm. The column temperature was set to 30° C. and the sample temperature was set to 25° C.

TABLE 3-2

| Time (min.) | Mobile phase B % |
|---|---|
| 0 | 0 |
| 2 | 0 |
| 47 | 20 |
| 49 | 20 |
| 54 | 100 |
| 56 | 0 |
| 66 | 0 |

The area of a hydrophilic peak detected by HIC, as an index of an oxidized form, was measured by an automatic analysts method to determine the amount (%) thereof. The amount is defined as percentage (%), by measuring the area of a hydrophilic peak detected b HIC by an automatic integration method and dividing it by the sum of all peak areas including the main peak. The main peak as used herein means the peak of the active body.

The evaluation results of HIC obtained in this Example are shown in FIG. 3-3.

TABLE 3-3

| Sample No. | HIC hydrophilic peak (%) |
|---|---|
| C1 | 23.30 |
| C2 | 26.40 |
| C3 | 19.18 |
| C4 | 23.84 |
| C5 | 19.70 |
| C6 | 40.72 |
| C7 | 23.34 |
| C8 | 21.07 |
| C9 | 20.70 |

In the preparations containing arginine (C2, C4, C6, and C7), a tendency to promote an increase in the HIC hydrophilic peak was observed in comparison with the preparations without arginine (C3 and C5) and preparatory containing sorbitol (C8 and C9).

In the preparation containing arginine of pH 7.0 (C6), a tendency to promote an increase in the HIC hydrophilic peak was observed in comparison with the preparation containing arginine of pH 6.0 (C4).

In the preparation containing histidine (C1), a tendency to promote an increase in the HIC hydrophilic peak was observed in comparison with the preparation containing phosphoric acid (C3).

Example 4: Study of Preparations by Design of Experiments Method

For liquid preparations containing antibody A, pH and arginine concentration were examined.

In this study, in order to evaluate the effects of arginine and pH, evaluation samples of sample Nos. D1 to D18 were prepared in accordance with design of experiments method. The formulation of each evaluation sample is shown in Tables 4-1 and 4-2 below.

TABLE 4-1

| Component | Function | D1 (/1 mL) | D2 (/1 mL) | D3 (/1 mL) | D4 (/1 mL) | D5 (/1 mL) |
|---|---|---|---|---|---|---|
| Antibody A | Active ingredient | 10 mg [approx. 0.07 mM] | 50 mg [approx. 0.3 mM] | 10 mg [approx. 0.07 mM] | 50 mg [approx. 0.3 mM] | 10 mg [approx. 0.07 mM] |
| $Na_2HPO_4 \cdot 12H_2O$ | Buffer | 7.16 mg [20 mM] | 7.16 mg [20 mM] | 7.16 mg [20 mM] | 7.16 mg [20 mM] | 7.16 mg [20 mM] |
| L-Histidine | Buffer | — | — | — | — | — |
| L-Arginine•HCl | Stabilizer | 58.98 mg [280 mM] | 58.98 mg [280 mM] | — | — | 58.98 mg [280 mM] |
| Polysorbate 80 | Surfactant | — | — | 0.40 mg [0.31 mM] (0.04 w/v %) | — | 0.40 mg [0.31 mM] (0.04 w/v %) |
| HCl | pH adjustor | adjusted to pH 6.5 | adjusted to pH 5.5 | adjusted to pH 6.5 | adjusted to pH 6.5 | adjusted to pH 5.5 |

| Component | Function | D6 (/1 mL) | D7 (/1 mL) | D8 (/1 mL) | D9 (/1 mL) |
|---|---|---|---|---|---|
| Antibody A | Active ingredient | 50 mg [approx. 0.3 mM] | 10 mg [approx. 0.07 mM] | 50 mg [approx. 0.3 mM] | 10 mg [approx. 0.07 mM] |
| $Na_2HPO_4 \cdot 12H_2O$ | Buffer | 7.16 mg [20 mM] | 7.16 mg [20 mM] | 7.16 mg [20 mM] | — |
| L-Histidine | Buffer | — | — | — | 3.10 mg [20 mM] |
| L-Arginine•HCl | Stabilizer | — | — | 58.98 mg [280 mM] | 58.98 mg [280 mM] |
| Polysorbate 80 | Surfactant | 0.40 mg [0.31 mM] (0.04 w/v %) | — | 0.40 mg [0.31 mM] (0.04 w/v %) | — |
| HCl | pH adjustor | adjusted to pH 5.5 | adjusted to pH 5.5 | adjusted to pH 6.5 | adjusted to pH 6.0 |

TABLE 4-2

| Component | Function | D10 (/1 mL) | D11 (/1 mL) | D12 (/1 mL) | D13 (/1 mL) | D14 (/1 mL) |
|---|---|---|---|---|---|---|
| Antibody A | Active ingredient | 50 mg [approx. 0.3 mM] | 10 mg [approx. 0.07 mM] | 50 mg [approx. 0.3 mM] | 10 mg [approx. 0.07 mM] | 50 mg [approx. 0.3 mM] |
| $Na_2HPO_4 \cdot 12H_2O$ | Buffer | — | — | — | — | — |
| L-Histidine | Buffer | 3.10 mg [20 mM] | 3.10 mg [20 mM] | 3.10 mg [20 mM] | 3.10 mg [20 mM] | 3.10 mg [20 mM] |
| L-Arginine•HCl | Stabilizer | 58.98 mg [280 mM] | — | — | 58.98 mg [280 mM] | — |
| Polysorbate 80 | Surfactant | — | 0.40 mg [0.31 mM] (0.04 w/v %) | — | 0.40 mg [0.31 mM] (0.04 w/v %) | 0.40 mg [0.31 mM] (0.04 w/v %) |
| HCl | pH adjustor | adjusted to pH 5.0 | adjusted to pH 6.0 | adjusted to pH 6.0 | adjusted to pH 5.0 | adjusted to pH 5.0 |

| Component | Function | D15 (/1 mL) | D16 (/1 mL) | D17 (/1 mL) | D18 (/1 mL) |
|---|---|---|---|---|---|
| Antibody A | Active ingredient | 10 mg [approx. 0.07 mM] | 50 mg [approx. 0.3 mM] | 30 mg [approx. 0.2 mM] | 30 mg [approx. 0.2 mM] |
| $Na_2HPO_4 \cdot 12H_2O$ | Buffer | — | — | 7.16 mg [20 mM] | — |
| L-Histidine | Buffer | 3.10 mg [20 mM] | 3.10 mg [20 mM] | — | 3.10 mg [20 mM] |
| L-Arginine•HCl | Stabilizer | — | 58.98 mg [280 mM] | 29.49 mg [140 mM] | 29.49 mg [140 mM] |
| Polysorbate 80 | Surfactant | — | 0.40 mg [0.31 mM] (0.04 w/v %) | 0.20 mg [0.15 mM] (0.02 w/v %) | 0.20 mg [0.15 mM] (0.02 w/v %) |
| HCl | pH adjustor | adjusted to pH 5.0 | adjusted to pH 6.0 | adjusted to pH 6.0 | adjusted to pH 5.5 |

In order to evaluate the stability of the liquid preparations, a thermal acceleration test (storage at 4° C. for 1 week) of each sample was performed. The purity of the antibody before and after the thermal acceleration was evaluated by size exclusion chromatography (SEC), ion exchange chromatography (IEC), and hydrophobic interaction chromatography (HIC). The analysis conditions are as follows.

Size Exclusion Chromatography (SEC)

A G3000 SWXL column for SEC (Tosoh) was connected to an HPLC system, and a mobile phase consisting of 20 mmol/L phosphoric acid and 1 mol/L NaCl pH 6.5 was flowed at a flow rate of 0.5 mL/min. Each sample was injected in an amount of 50 μg in terms of protein. The analysis time was 40 minutes, and the detection was carried out at UV 280 nm. The column temperature was set to 30° C., and the sample temperature was set to 5° C.

Ion Exchange Chromatography (IEC)

A Propac WCX 10 column for IEC (Dionex) was connected to an HPLC system. A mobile phase consisting of 25 mmol/L phosphoric acid pH 6.0 was connected to a mobile phase A line, and a mobile phase consisting of 25 mmol/L phosphoric acid and 500 mmol/L NaCl pH 6.0 was connected to a mobile phase B line, and the mobile phases were flowed at a flow rate of 1 mL/min. The samples were diluted to 1 mg/mL with the mobile phase A, and 10 μL was injected. The analysis time was 80 minutes, and the IEC gradient program of Table 4-3 was applied. The detection was carried out at UV 280 nm. The column temperature was set to 35° C., and the sample temperature set to 5° C.

TABLE 4-3

| Time (min.) | Mobile phase B % |
|---|---|
| 0 | 10 |
| 5 | 10 |
| 55 | 35 |
| 55.1 | 100 |
| 65 | 100 |
| 65.1 | 10 |
| 80 | 10 |

Hydrophobic Interaction Chromatography (HIC)

Two ProPac HIC-10 columns for HIC (Dionex) were connected to an HPLC system. A mobile phase consisting of 800 mmol/L ammonium sulfate and 20 mmol/L sodium phosphate pH7.0 was connected to a mobile phase A line, and a mobile phase consisting of 20 mmol/L sodium phosphate pH7.0 was connected to a mobile phase B line, and the mobile phases were flowed at a flow rate of 0.8 mL/min. The samples were diluted to 1 mg/ml with the mobile phase A, and 50 μL was injected. The HIC gradient program of Table 4-4 was applied. The detection was carried out at UV 280 nm. The column temperature was set to 30° C., and the sample temperature was set to 25° C.

TABLE 4-4

| Time (min.) | Mobile phase B % |
|---|---|
| 0 | 0 |
| 2 | 0 |
| 47 | 20 |
| 49 | 20 |
| 54 | 100 |
| 56 | 0 |
| 66 | 0 |

The areas of multimer peaks and degradant peaks detected by SEC, the area of the main peak detected by IEC, and the area of a hydrophilic peak detected by HIC were measured by an automatic analysis method to determine the amounts (%) thereof. The amounts are defined as percentage (%), by measuring the area of multimer peaks or degradant peaks detected by SEC by automatic analysis method and dividing it by the sum of all peak areas including the main peak, by measuring the area of the main peak detected by IEC by an automatic analysis method and dividing it by the sum of all peak areas other than the main peak, or by measuring the area of a hydrophilic peak detected by HIC by an automatic integration method and dividing it by the sum of all peak areas including the main peak. The main peak as used herein means the peak of the active body.

Figures 1, 4:
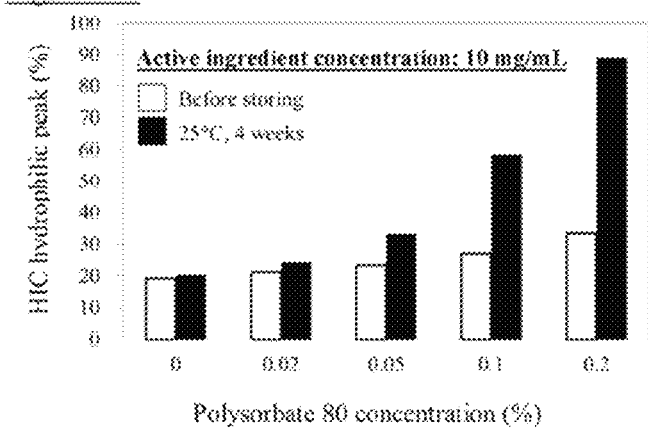
Figures 2, 4:
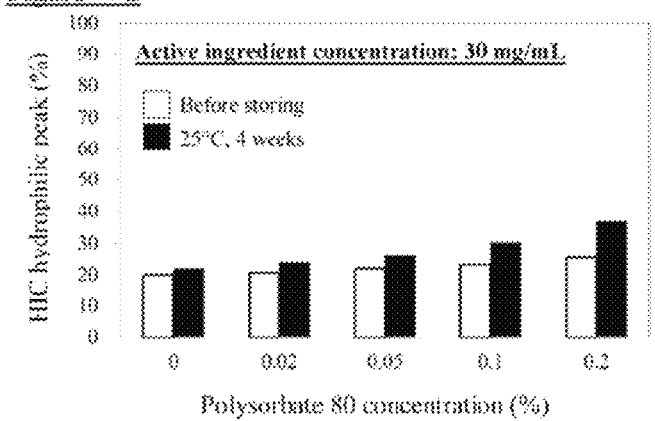
Figure 5:
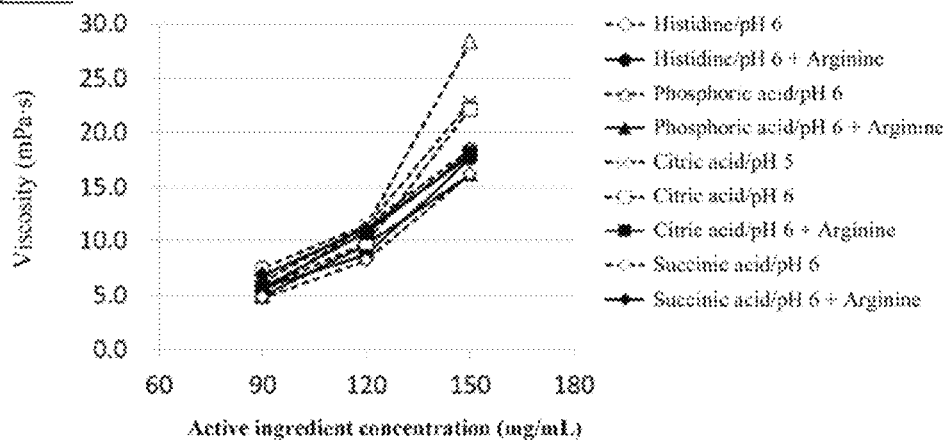
FIG. 5 shows the evaluation results of viscosity obtained in Example 6.

The evaluation results of SEC, IEC, and HIC obtained in this Example are shown in FIG. 4-5.

TABLE 4-5

| Sample | SEC Multimer % | | SEC Degradant % | | IEC Main peak % | | HIC Hydrophillic peak % | |
|---|---|---|---|---|---|---|---|---|
| No. | Initial | 40° C. 1 W | Initial | 40° C. 1 W | Initial | 40° C. 1 W | Initial | 40° C. 1 W |
| D1 | 2.18 | 1.56 | 1.12 | 1.90 | 59.30 | 55.85 | 14.83 | 22.51 |
| D2 | 2.06 | 1.40 | 1.11 | 2.07 | 60.34 | 57.98 | 15.14 | 17.76 |
| D3 | 2.78 | 2.41 | 1.10 | 1.71 | 60.99 | 54.46 | 15.58 | 20.20 |
| D4 | 3.41 | 3.88 | 1.07 | 1.68 | 60.15 | 55.16 | 15.05 | 17.38 |
| D5 | 1.98 | 1.22 | 1.09 | 1.97 | 60.28 | 57.44 | 15.96 | 22.55 |
| D6 | 2.68 | 2.37 | 1.10 | 1.78 | 60.41 | 56.11 | 15.64 | 17.08 |
| D7 | 2.13 | 1.54 | 1.13 | 1.85 | 59.68 | 55.39 | 15.20 | 15.68 |
| D8 | 2.40 | 1.92 | 1.11 | 1.89 | 60.07 | 55.42 | 15.81 | 28.49 |
| D9 | 2.14 | 1.23 | 1.20 | 1.74 | 59.67 | 59.40 | 15.43 | 17.70 |
| D10 | 1.92 | 1.17 | 1.36 | 3.16 | 59.90 | 57.08 | 15.42 | 16.57 |
| D11 | 2.01 | 1.04 | 1.17 | 1.65 | 59.48 | 58.54 | 15.97 | 21.07 |
| D12 | 2.35 | 1.67 | 1.15 | 1.73 | 60.04 | 56.96 | 15.26 | 17.65 |
| D13 | 1.88 | 0.90 | 1.19 | 3.06 | 58.93 | 54.89 | 16.35 | 25.35 |
| D14 | 2.09 | 1.23 | 1.29 | 2.22 | 59.18 | 54.72 | 15.79 | 17.35 |
| D15 | 1.90 | 0.92 | 1.26 | 1.98 | 59.16 | 54.91 | 15.40 | 15.60 |
| D16 | 2.20 | 1.51 | 1.18 | 1.92 | 59.03 | 57.39 | 15.96 | 21.46 |
| D17 | 2.25 | 1.84 | 1.19 | 1.78 | 59.01 | 56.49 | 15.78 | 20.13 |
| D18 | 2.12 | 1.31 | 1.17 | 2.35 | 58.97 | 56.16 | 15.77 | 18.02 |

Statistical analysis of factor screening was conducted based on the results, and p-values indicating the degree of contribution of each index were calculated using design of experiments software, Design-Expert (a product of Stat-Ease, Inc.). The results are shown in Table 4-6.

TABLE 4-6

| | SEC Multimer % | SEC Degradant % increased | IEC Main peak % decreased | HIC Hydrophilic peak % increased |
|---|---|---|---|---|
| Phosphate buffer formulation: | | | | |
| Antibody A concentration | 0.0262 | 0.0996 | 0.0370 | 0.4252 |
| Polysorbate 80 concentration | 0.3347 | 0.1273 | NA | 0.1011 |
| pH | 0.0377 | 0.0025 | 0.0027 | NA |
| Arginine concentration | 0.8577 | 0.0044 | 0.0157 | 0.2734 |
| Histidine buffer formulation: | | | | |
| Antibody A concentration | 0.0262 | 0.0996 | 0.0370 | 0.4252 |
| Polysorbate 80 concentration | 0.3347 | 0.1273 | NA | 0.1011 |
| pH | 0.0377 | 0.0025 | 0.0027 | NA |
| Arginine concentration | 0.8577 | 0.0044 | 0.0157 | 0.2734 |

*NA: not assayed

From the results, with respect to all the evaluation items of SEC, IEC, and HIC as an index of stability, the range of maximizing the desirability for arginine concentration and pH, which contributed greatly to the stabilizing effect, was analyzed using design of experiments software, Design-Expert (a product of Stat-Ease, Inc.). The results are shown in FIG. 3-1 (a group of phosphoric acid-containing formulations) and FIG. 3-2 (a group of histidine-containing formulations).

It was suggested from the results that the antibody was stable in the range of pH 5.5 to 5.7 and an arginine concentration range of 0 to 210 mmol/L (excluding no addition) in the phosphoric acid-containing formulations, and that the antibody was stable in the range of pH 5.3 to 6.0 and an arginine concentration range of 0 to 210 mmol/L (excluding no addition) the histidine-containing formulations.

Example 5: Suppression of Generation of Insoluble Microparticles by Surfactant

For liquid preparations containing antibody A, the suppression effect of surfactants on generation of insoluble microparticles after stress loading was evaluated.

In this study, in order to evaluate the effects of polysorbate 80, polysorbate 20, and poloxamer 188 (Pluronic F68), which were surfactants, evaluation samples of sample Nos, E1 to E18 were prepared. The formulation of each evaluation, sample is shown in Tables 5-1 and 5-2 below,

TABLE 5-1

| Component | Function | E1 (/1 mL) | E2 (/1 mL) | E3 (/1 mL) | E4 (/1 mL) | E5 (/1 mL) |
|---|---|---|---|---|---|---|
| Antibody A | Active ingredient | 10 mg [approx. 0.07 mM] | 10 mg [approx. 0.07 mM] | 10 mg [approx. 0.07 mM] | 10 mg [approx. 0.07 mM] | 10 mg [approx. 0.07 mM] |
| L-Histidine | Buffer | 3.10 mg [20 mM] | 3.10 mg [20 mM] | 3.10 mg [20 mM] | 3.10 mg [20 mM] | 3.10 mg [20 mM] |
| L-Arginine•HCl | Stabilizer | 29.49 mg [140 mM] | 29.49 mg [140 mM] | 29.49 mg [140 mM] | 29.49 mg [140 mM] | 29.49 mg [140 mM] |
| Polysorbate 80 | Surfactant | — | 0.20 mg [0.15 mM] (0.02 w/v %) | 0.50 mg [0.38 mM] (0.05 w/v %) | 1.00 mg [0.76 mM] (0.10 w/v %) | 2.00 mg [1.53 mM] (0.20 w/v %) |
| Polysorbate 20 | Surfactant | — | — | — | — | — |
| Poloxamer 188 | Surfactant | — | — | — | — | — |
| HCl | pH adjustor | adjusted to pH 6.0 | adjusted to pH 6.0 | adjusted to pH 6.0 | adjusted to pH 6.0 | adjusted to pH 6.0 |
| Component | Function | E6 (/1 mL) | E7 (/1 mL) | E8 (/1 mL) | E9 (/1 mL) | |
| Antibody A | Active ingredient | 30 mg [approx. 0.2 mM] | 30 mg [approx. 0.2 mM] | 30 mg [approx. 0.2 mM] | 30 mg [approx. 0.2 mM] | |
| L-Histidine | Buffer | 3.10 mg [20 mM] | 3.10 mg [20 mM] | 3.10 mg [20 mM] | 3.10 mg [20 mM] | |
| L-Arginine•HCl | Stabilizer | 29.49 mg [140 mM] | 29.49 mg [140 mM] | 29.49 mg [140 mM] | 29.49 mg [140 mM] | |
| Polysorbate 80 | Surfactant | — | 0.20 mg [0.15 mM] (0.02 w/v %) | 0.50 mg [0.38 mM] (0.05 w/v %) | 1.00 mg [0.76 mM] (0.10 w/v %) | |
| Polysorbate 20 | Surfactant | — | — | — | — | |
| Poloxamer 188 | Surfactant | — | — | — | — | |
| HCl | pH adjustor | adjusted to pH 6.0 | adjusted to pH 6.0 | adjusted to pH 6.0 | adjusted to pH 6.0 | |

TABLE 5-2

| Component | Function | E10 (/1 mL) | E11 (/1 mL) | E12 (/1 mL) | E13 (/1 mL) | E14 (/1 mL) |
|---|---|---|---|---|---|---|
| Antibody A | Active ingredient | 30 mg [approx. 0.2 mM] | 10 mg [approx. 0.07 mM] | 30 mg [approx. 0.2 mM] | 10 mg [approx. 0.07 mM] | 10 mg [approx. 0.07 mM] |

TABLE 5-2-continued

| Component | Function | | | | | |
|---|---|---|---|---|---|---|
| L-Histidine | Buffer | 3.10 mg [20 mM] | 3.10 mg [20 mM] | 3.10 mg [20 mM] | 3.10 mg [20 mM] | 3.10 mg [20 mM] |
| L-Arginine•HCl | Stabilizer | 29.49 mg [140 mM] | 29.49 mg [140 mM] | 29.49 mg [140 mM] | 29.49 mg [140 mM] | 29.49 mg [140 mM] |
| Polysorbate 80 | Surfactant | 2.00 mg [1.53 mM] (0.20 w/v %) | — | — | — | — |
| Polysorbate 20 | Surfactant | — | 0.20 mg [0.16 mM] (0.02 w/v %) | 0.20 mg [0.16 mM] (0.02 w/v %) | — | — |
| Poloxamer 188 | Surfactant | — | — | — | 0.20 mg [0.02 mM] (0.02 w/v %) | 0.50 mg [0.06 mM] (0.05 w/v %) |
| HCl | pH adjustor | adjusted to pH 6.0 | adjusted to pH 6.0 | adjusted to pH 6.0 | adjusted to pH 6.0 | adjusted to pH 6.0 |

| Component | Function | E15 (/1 mL) | E16 (/1 mL) | E17 (/1 mL) | E18 (/1 mL) |
|---|---|---|---|---|---|
| Antibody A | Active ingredient | 10 mg [approx. 0.07 mM] | 30 mg [approx. 0.2 mM] | 30 mg [approx. 0.2 mM] | 30 mg [approx. 0.2 mM] |
| L-Histidine | Buffer | 3.10 mg [20 mM] | 3.10 mg [20 mM] | 3.10 mg [20 mM] | 3.10 mg [20 mM] |
| L-Arginine•HCl | Stabilizer | 29.49 mg [140 mM] | 29.49 mg [140 mM] | 29.49 mg [140 mM] | 29.49 mg [140 mM] |
| Polysorbate 80 | Surfactant | — | — | — | — |
| Polysorbate 20 | Surfactant | — | — | — | — |
| Poloxamer 188 | Surfactant | 1.00 mg [0.12 mM] (0.10 w/v %) | 0.20 mg [0.02 mM] (0.02 w/v %) | 0.50 mg [0.06 mM] (0.05 w/v %) | 1.00 mg [0.12 mM] (0.10 w/v %) |
| HCl | pH adjustor | adjusted to pH 6.0 | adjusted to pH 6.0 | adjusted to pH 6.0 | adjusted to pH 6.0 |

In order to evaluate the stability of liquid preparations, each sample was subjected to a stress load test. For each sample, three freeze-thaw cycles between −80° C. and 5° C. were carried out, and samples were shaken at 150 rpm for 24 hours and stored under 1,000 lux for 24 hours. The number of insoluble microparticles in each sample after stress loading was evaluated by light obscuration particle counting.

Light Obscuration Particle Counting

After 0.7 mL of a sample was placed in a 1.5 mL plastic tube, it was degassed for 2 hours under conditions of 25° C. and 75 Torr using a vacuum dryer. After degassing, measurement was carried out using a HIAC liquid particle counter for laboratories, with the setting of a tare volume of 0.2 mL, a sampling volume of 0.2 mL and a Run cycle of 2 (the first measurement was discarded).

In order to evaluate the influence of the surfactant concentration and the active ingredient concentration on the protein, with respect to samples E1 to E10, the samples were stored at 25° C. for 4 weeks, and the samples after storage were evaluated by hydrophobic interaction chromatography (HIC).

Hydrophobic Interaction Chromatography (HIC)

Two ProPac HIC-10 columns for HIC (Dionex) were connected to an HPLC system. A mobile phase consisting of 800 mmol/L ammonium sulfate and 20 mmol/L sodium phosphate pH7.0 was connected to a mobile phase A line, and a mobile phase consisting of 20 mmol/L sodium phosphate pH7.0 was connected to a mobile phase B line, and the mobile phases were flowed at a flow rate of 0.8 ml/min. The samples were diluted in 1 mg/mL with the mobile phase A, and 50 μL was injected. The HIC gradient program of Table 5-3 was applied. The detection was carried out at UV 280 nm. The column temperature was set to 30° C. and the sample temperature was set to 25° C.

TABLE 5-3

| Time (min.) | Mobile phase B % |
|---|---|
| 0 | 0 |
| 2 | 0 |
| 47 | 20 |
| 49 | 20 |
| 54 | 100 |
| 56 | 0 |
| 66 | 0 |

The area of the hydrophilic peak detected by HIC was measured by an automatic analysis method to determine the amount (%) thereof. The amount is defined as percentage (%), by measuring the area of the hydrophilic peak detected in HIC by an automatic integration method and dividing it by the sum of all peak areas including the main peak. The main peak as used herein means the peak of the active body.

The evaluation results of the numbers of insoluble microparticles obtained in this Example are shown in Table 5-4. Whether or not a surfactant is added, an increase in the number of insoluble microparticles after stress loading was observed, but the increase in the number of insoluble microparticles was suppressed in all samples added with a surfactant.

TABLE 5-4

| Sample No. | Buffer/Additive/pH | Active ingredient concentration | Surfactant/ Concentration added | Before stress load (particles/mL) | After Stress load (particles/mL) |
|---|---|---|---|---|---|
| E1 | 20 mM Histidine/ | 10 mg/mL | Polysorbate 80/0% | 190 | 23285 |
| E2 | 140 mM Arginine/pH 6.0 | | Polysorbate 80/0.02% | 195 | 3065 |
| E3 | | | Polysorbate 80/0.05% | 105 | 640 |
| E4 | | | Polysorbate 80/0.10% | 225 | 780 |
| E5 | | | Polysorbate 80/0.20% | 140 | 935 |
| E6 | | 30 mg/mL | Polysorbate 80/0% | 180 | 22145 |
| E7 | | | Polysorbate 80/0.02% | 45 | 2480 |
| E8 | | | Polysorbate 80/0.05% | 65 | 790 |
| E9 | | | Polysorbate 80/0.10% | 65 | 720 |
| E10 | | | Polysorbate 80/0.20% | 90 | 335 |
| E11 | | 10 mg/mL | Polysorbate 20/0.02% | 505 | 990 |
| E12 | | 30 mg/mL | Polysorbate 20/0.02% | 150 | 1190 |
| E13 | | 10 mg/mL | Poloxamer 188/0.02% | 385 | 965 |
| E14 | | | Poloxamer 188/0.05% | 115 | 1075 |
| E15 | | | Poloxamer 188/0.10% | 125 | 845 |
| E16 | | 30 mg/mL | Poloxamer 188/0.02% | 135 | 4630 |
| E17 | | | Poloxamer 188/0.05% | 85 | 1500 |
| E18 | | | Poloxamer 188/0.10% | 185 | 2750 |

The evaluation results of HIC obtained in this Example are shown in FIGS. 4-1 and 4-2. For the samples containing polysorbate 80, an increasing tendency of the HIC hydrophilic peak was observed with increasing the concentration of polysorbate 80. On the other hand, for the samples containing the active ingredient at a concentration of 30 mg/mL (FIG. 4-2), the increase in the HIC hydrophilic peak was suppressed in comparison with the samples containing the active ingredient at a concentration of 10 mg/mL (FIG. 4-1).

Example 6: Reduction of Viscosity by Arginine

For liquid preparations containing antibody A, the effect of reducing the viscosity by arginine as evaluated.

In this study, in order to evaluate the effect of arginine on the viscosity of liquid preparations, evaluation samples of sample Nos. F1 to F12 were prepared. The formulation of each evaluation sample is shown in Table 6-1 below.

TABLE 6-1

| Component | Function | F1 (/1 mL) | F2 (/1 mL) | F3 (/1 mL) | F4 (/1 mL) | F5 (/1 mL) |
|---|---|---|---|---|---|---|
| Antibody A | Active ingredient | 150 mg [approx. 1.0 mM] | 120 mg [approx. 0.8 mM] | 90 mg [approx. 0.6 mM] | 150 mg [approx. 1.0 mM] | 120 mg [approx. 0.8 mM] |
| L-Histidine | Buffer | 3.10 mg [20 mM] | 3.10 mg [20 mM] | 3.10 mg [20 mM] | — | — |
| Na$_2$HPO$_4$·12H$_2$O | Buffer | — | — | — | 7.16 mg [20 mM] | 7.16 mg [20 mM] |
| Citric acid | Buffer | — | — | — | — | — |
| Succinic acid | Buffer | — | — | — | — | — |
| L-Arginine·HCl | Stabilizer | 29.49 mg [140 mM] | 29.49 mg [140 mM] | 29.49 mg [140 mM] | 29.49 mg [140 mM] | 29.49 mg [140 mM] |
| HCl | pH adjustor | adjusted to pH 6.0 | adjusted to pH 6.0 | adjusted to pH 6.0 | adjusted to pH 6.0 | adjusted to pH 6.0 |
| NaOH | pH adjustor | | | | | |

| Component | Function | F6 (/1 mL) | F7 (/1 mL) | F8 (/1 mL) | F9 (/1 mL) | F10 (/1 mL) |
|---|---|---|---|---|---|---|
| Antibody A | Active ingredient | 90 mg [approx. 0.6 mM] | 150 mg [approx. 1.0 mM] | 120 mg [approx. 0.8 mM] | 90 mg [approx. 0.6 mM] | 150 mg [approx. 1.0 mM] |
| L-Histidine | Buffer | — | — | — | — | — |
| Na$_2$HPO$_4$·12H$_2$O | Buffer | 7.16 mg [20 mM] | — | — | — | — |
| Citric acid | Buffer | — | 3.84 mg [20 mM] | 3.84 mg [20 mM] | 3.84 mg [20 mM] | — |
| Succinic acid | Buffer | — | — | — | — | 2.36 mg [20 mM] |
| L-Arginine·HCl | Stabilizer | 29.49 mg [140 mM] | 29.49 mg [140 mM] | 29.49 mg [140 mM] | 29.49 mg [140 mM] | 29.49 mg [140 mM] |
| HCl | pH adjustor | adjusted to pH 6.0 | adjusted to pH 6.0 | adjusted to pH 6.0 | adjusted to pH 6.0 | adjusted to pH 6.0 |
| NaOH | pH adjustor | | | | | |

| Component | Function | F11 (/1 mL) | F12 (/1 mL) |
|---|---|---|---|
| Antibody A | Active ingredient | 120 mg [approx. 0.8 mM] | 90 mg [approx. 0.6 mM] |

TABLE 6-1-continued

| | | | |
|---|---|---|---|
| L-Histidine | Buffer | — | — |
| Na$_2$HPO$_4$•12H$_2$O | Buffer | — | — |
| Citric acid | Buffer | — | — |
| Succinic acid | Buffer | 2.36 mg [20 mM] | 2.36 mg [20 mM] |
| L-Arginine•HCl | Stabilizer | 29.49 mg [140 mM] | 29.49 mg [140 mM] |
| HCl | pH adjustor | adjusted to | adjusted to |
| NaOH | pH adjustor | pH 6.0 | pH 6.0 |

Comparative Example 2

In order to evaluate the effects of arginine and pH evaluation samples without arginine (sample Nos. F13 to F27) and evaluation samples at a low pH (sample Nos. F19 to F21) were prepared. The formulation of each evaluation sample is shown in Table 6-2 below.

TABLE 6-2

| Component | Function | F13 (/1 mL) | F14 (/1 mL) | F15 (/1 mL) | F16 (/1 mL) | F17 (/1 mL) |
|---|---|---|---|---|---|---|
| Antibody A | Active ingredient | 150 mg [approx. 1.0 mM] | 120 mg [approx. 0.8 mM] | 90 mg [approx. 0.6 mM] | 150 mg [approx. 1.0 mM] | 120 mg [approx. 0.8 mM] |
| L-Histidine | Buffer | 3.10 mg [20 mM] | 3.10 mg [20 mM] | 3.10 mg [20 mM] | — | — |
| Na$_2$HPO$_4$•12H$_2$O | Buffer | — | — | — | 7.16 mg [20 mM] | 7.16 mg [20 mM] |
| Citric acid | Buffer | — | — | — | — | — |
| Succinic acid | Buffer | — | — | — | — | — |
| HCl | pH adjustor | adjusted to | adjusted to | adjusted to | adjusted to | adjusted to |
| NaOH | pH adjustor | pH 6.0 | pH 6.0 | pH 6.0 | pH 6.0 | pH 6.0 |

| Component | Function | F18 (/1 mL) | F19 (/1 mL) | F20 (/1 mL) | F21 (/1 mL) | F22 (/1 mL) |
|---|---|---|---|---|---|---|
| Antibody A | Active ingredient | 90 mg [approx. 0.6 mM] | 150 mg [approx. 1.0 mM] | 120 mg [approx. 0.8 mM] | 90 mg [approx. 0.6 mM] | 150 mg [approx. 1.0 mM] |
| L-Histidine | Buffer | — | — | — | — | — |
| Na$_2$HPO$_4$•12H$_2$O | Buffer | 7.16 mg [20 mM] | — | — | — | — |
| Citric acid | Buffer | — | 3.84 mg [20 mM] | 3.84 mg [20 mM] | 3.84 mg [20 mM] | 3.84 mg [20 mM] |
| Succinic acid | Buffer | — | — | — | — | — |
| HCl | pH adjustor | adjusted to | adjusted to | adjusted to | adjusted to | adjusted to |
| NaOH | pH adjustor | pH 6.0 | pH 5.0 | pH 5.0 | pH 5.0 | pH 6.0 |

| Component | Function | F23 (/1 mL) | F24 (/1 mL) | F25 (/1 mL) | F26 (/1 mL) | F27 (/1 mL) |
|---|---|---|---|---|---|---|
| Antibody A | Active ingredient | 120 mg [approx. 0.8 mM] | 90 mg [approx. 0.6 mM] | 150 mg [approx. 1.0 mM] | 120 mg [approx. 0.8 mM] | 90 mg [approx. 0.6 mM] |
| L-Histidine | Buffer | — | — | — | — | — |
| Na$_2$HPO$_4$•12H$_2$O | Buffer | — | — | — | — | — |
| Citric acid | Buffer | 3.84 mg [20 mM] | 3.84 mg [20 mM] | — | — | — |
| Succinic acid | Buffer | — | — | 2.36 mg [20 mM] | 2.36 mg [20 mM] | 2.36 mg [20 mM] |
| HCl | pH adjustor | adjusted to | adjusted to | adjusted to | adjusted to | adjusted to |
| NaOH | pH adjustor | pH 6.0 | pH 6.0 | pH 6.0 | pH 6.0 | pH 6.0 |

For the prepared samples of Tables 6-1 and 6-2, the viscosity was evaluated by dynamic light scattering (DLS).

Dynamic Light Scattering (DLS)

A standard curve of viscosity-apparent particle radius was prepared from apparent particle radii obtained by adding polystyrene particles to glycerin solutions of 50%, 60%, 65%, 70%, and 75%, using DynaPro Platereader (Wyatt). Next, an apparent radius was measured by adding, polystyrene particles to a high concentration sample, and the viscosity was calculated from the standard cure of glycerin solutions.

The range of viscosity is desired to be controlled to 1000 mPa·s or less, preferably 100 mPa·s or less, and more preferably 20 mPa·s or less.

The evaluation results of viscosity obtained in this Example and Comparative Example are shown in Table 6-3 and FIG. 5, For the samples added with arginine, an increase in the viscosity accompanying the increase in the concentration of the active ingredient was suppressed.

On the other hand, the influence of pH on viscosity was not observed.

TABLE 6-3

| Sample No. | Active ingredient concentration | Buffer/pH | Additive | Viscosity (mPa · s) |
|---|---|---|---|---|
| F13 | 150 mg/mL | 20 mM L-Histidine/pH 6 | — | 18.4 |
| F14 | 120 mg/mL | | | 11.4 |
| F15 | 90 mg/mL | | | 7.5 |
| F1 | 150 mg/mL | | 140 mM Arginine-HCl | 17.7 |
| F2 | 120 mg/mL | | | 8.7 |
| F3 | 90 mg/mL | | | 5.7 |
| F16 | 150 mg/mL | 20 mM Phosphoric acid/pH 6 | — | 28.4 |
| F17 | 120 mg/mL | | | 11.3 |
| F18 | 90 mg/mL | | | 6.3 |
| F4 | 150 mg/mL | | 140 mM Arginine-HCl | 16.2 |
| F5 | 120 mg/mL | | | 9.7 |
| F6 | 90 mg/mL | | | 5.0 |
| F19 | 150 mg/mL | 20 mM Citric acid/pH 5 | — | 22.8 |
| F20 | 120 mg/mL | | | 11.4 |
| F21 | 90 mg/mL | | | 5.3 |
| F22 | 150 mg/mL | 20 mM Citric acid/pH 6 | — | 22.2 |
| F23 | 120 mg/mL | | | 9.8 |
| F24 | 90 mg/mL | | | 5.7 |
| F7 | 150 mg/mL | | 140 mM Arginine-HCl | 18.1 |
| F8 | 120 mg/mL | | | 10.7 |
| F9 | 90 mg/mL | | | 5.7 |
| F25 | 150 mg/mL | 20 mM Succinic acid/pH 6 | — | 16.2 |
| F26 | 120 mg/mL | | | 8.2 |
| F27 | 90 mg/mL | | | 4.8 |
| F10 | 150 mg/mL | | 140 mM Arginine-HCl | 17.9 |
| F11 | 120 mg/mL | | | 11.1 |
| F12 | 90 mg/mL | | | 6.9 |

Example 7: Stability Evaluation

For a liquid preparation containing antibody A, the stability was evaluated. The formulation of the evaluation sample is shown in Table 7-1 below. The evaluation sample was prepared by, after cultivation and purification, carrying out buffer exchange to the formulation of Table 7-1, diluting the obtained protein drug solution with a solution containing the components other than antibody A described in Table 7-1, filtering it through a 0.22 μm filter, filling a glass vial with the filtrate, and carrying out capping and tightening.

TABLE 7-1

| Component | Function | G1 (/1 mL) |
|---|---|---|
| Antibody A | Active ingredient | 30 mg [approx. 0.21 mM] |
| Na$_2$HPO$_4$•12H$_2$O | Buffer | 0.82 mg [2 mM] (pH 5.7) |
| NaH$_2$PO$_4$•2H$_2$O | Buffer | 2.76 mg [18 mM] (pH 5.7) |
| L-Arginine•HCl | Stabilizer | 29.49 mg [140 mM] |
| Polysorbate 80 | Surfactant | 0.20 mg [0.15 mM] (0.02 w/v %) |

In order to evaluate the stability of the liquid preparation, a storage stability test (at −20° C. for 12 months and at 5° C. for 12 months) of the sample was carried out. The quality of the antibody before and after the storage was evaluated by size exclusion chromatography (SEC), ion exchange chromatography (IEC), and hydrophobic interaction chromatography (HIC). The analysts conditions are as follows.

Size Exclusion Chromatography (SEC)

A TSK guard column SWXL (Tosoh) and two G3000 SWXL columns for SEC (Tosoh) sequentially connected were connected to an HPLC system, and a mobile phase consisting of 20 mmol/L phosphoric acid and 1 mol/L NaCl pH 6.5 was flowed at a flow rate of 0.5 mL/min. Each sample was injected in an amount of 50 μg in terms of protein. The analysis time was 60 minutes, and the detection was carried out at UV 280 nm. The column temperature was set to 30° C., and the sample temperature was set to 5° C.

Ion Exchange Chromatography (IEC)

A MabPac SCX10 column for IEC (Thermo) was connected to an HPLC system. A mobile phase consisting of 25 mmol/L MES pH 6.0 was connected to a mobile phase A line, and a mobile phase consisting of 25 mmol/L MES and 500 mmol/L NaCl pH 6.0 was connected to a mobile phase B line, and the mobile phases were flowed at a flow rate of 1 mL/min. The samples were diluted to 1 mg/mL, with the mobile phase A, and 10 μL was injected. The analysis time was 70 minutes, and the IEC gradient program of Table 7-2 was applied. The detection was carried out at UV 280 nm. The column temperature was set to 35° C. and the sample temperature was set to 5° C.

TABLE 7-2

| Time (min.) | Mobile phase B % |
|---|---|
| 0 | 15 |
| 5 | 15 |
| 50 | 30 |
| 50.1 | 100 |
| 60 | 100 |
| 60.1 | 15 |
| 70 | 15 |

Hydrophobic Interaction Chromatography (HIC)

Two ProPac HIC-10 columns for HIC (Dionex) were connected to an HPLC system. A mobile phase consisting of 800 mmol/L ammonium sulfate and 20 mmol/L sodium phosphate pH7.0 was connected to a mobile phase A line, and a mobile phase consisting of 20 mmol/L sodium phosphate pH7.0 was connected to a mobile phase B line, and the mobile phases were flowed at a flow rate of 0.8% mL/min. The samples were diluted to 1 mg/mL with the mobile phase A, and 50 λL was injected. The HIC gradient program of Table 7-3 was applied. The detection was carried out at UV 280 nm. The column temperature was set to 30° C., and the sample temperature was set to 25° C.

TABLE 7-3

| Time (min.) | Mobile phase B % |
|---|---|
| 0 | 0 |
| 2 | 0 |
| 47 | 20 |
| 49 | 20 |
| 54 | 100 |
| 56 | 0 |
| 66 | 0 |

The areas of multimer peaks and degradant peaks detected by SEC, the area of the main peak detected by IEC, and the area of a hydrophilic peak detected by HIC were measured by an automatic analysis method to determine the amounts (%) thereof. The amounts are defined as percentage (%), by measuring the area of multimer peaks or degradant peaks detected by SEC by an automatic analysis method and dividing it by the sum of all peak areas including the main peak, by measuring the area of the main peak detected by IPC by an automatic analysis method and dividing it by the sum of all peak areas other than the main peak, or by measuring the area of a hydrophilic peak detected by HIC by an automatic integration method and dividing it by the sum of all peak areas including the main peak. The main peak as used herein means the peak of the active body.

The evaluation results of SEC, IEC, and HIC obtained in this Example are shown in Table 7-4. In this formulation, in both cases of the storage at −20° C. for 12 months and at 5° C. for 12 months, the quality in each index was within a suitable range, and if was confirmed that this formulation was stable.

TABLE 7-4

| Evaluation index | Initial | Storage conditions | |
| --- | --- | --- | --- |
| | | −20° C. 12 months | 5° C. 12 months |
| SEC Multimer % | 0.68 | 0.94 | 1.81 |
| SEC Degradant % | 1.07 | 0.76 | 1.91 |
| IEC Main peak % | 69.36 | 67.94 | 58.76 |
| HIC Hydrophilic peak % | 11.24 | 11.70 | 26.49 |

INDUSTRIAL APPLICABILITY

According to the present invention, a stable pharmaceutical composition comprising an anti-human TSLP receptor antibody, more particularly, a stable pharmaceutical composition comprising an anti-human TSLP receptor antibody, which suppresses the generation of chemically modified substances, such as deamidated forms and oxidized forms, or degradants or multimers, can be provided.

Although the present invention has been described with reference to specific embodiments, various changes and modification obvious to those skilled in the an are possible without departing from the scope of the appended claims.

Free Text in Sequence Listing

Features of "Artificial Sequence" are described in the numeric identifier <223> in the Sequence Listing. The nucleotide sequences of SEQ ID NOs: 2 and 4 in the Sequence listing are ones of the H-chain and the L-chain of the anti-human TSLP Receptor antibody, respectively. The amino acid sequences of SEQ ID NOs: 1 and 3 are ones of the H-chain and the L-chain encoded by SEO ID NOs: 2 and 4, respectively.

The invention claimed is:

1. A stable pharmaceutical composition comprising an anti-human TSLP receptor antibody, a pharmaceutically acceptable buffer, arginine or a pharmaceutically acceptable salt thereof, and a surfactant, wherein the following (1) and/or (2) is contained as the anti-human TSLP receptor antibody:
  (1) an anti-human TSLP receptor antibody comprising a heavy chain consisting of the amino acid sequence of SEQ ID NO: 1, and a light chain consisting of the amino acid sequence of SEQ ID NO: 3, and
  (2) an anti-human TSLP receptor antibody consisting of amino acid sequences of an antibody generated by a post-translational modification of the anti-human TSLP receptor antibody of (1),
  wherein the post-translational modification is a pyroglutamylation at the N-terminus of a heavy chain variable region and/or lysine deletion at the C-terminus of a heavy chain,
  wherein a concentration of the arginine or a pharmaceutically acceptable salt thereof is 700 mmol/L or less,
  wherein the pharmaceutical composition is a liquid preparation, or a lyophilized preparation or a spray-dried preparation,
  wherein when the pharmaceutical composition is a liquid preparation, a content of the anti-human TSLP receptor antibody is 0.007 to 2 mmol/L, or when the pharmaceutical composition is a lyophilized preparation or a spray-dried preparation, a content of a solution after reconstituting the preparation in water is 0.007 to 2 mmol/L, and
  wherein when the pharmaceutical composition is a liquid preparation, a pH of the liquid preparation is 5 to 6, or when the pharmaceutical composition is a lyophilized preparation or a spray-dried preparation, a pH of a solution after reconstituting the preparation in water is 5 to 6.

2. The pharmaceutical composition according to claim 1, wherein the pharmaceutically acceptable buffer is one, or two or more selected from the group consisting of phosphoric acid, citric acid, acetic acid, succinic acid, histidine, ascorbic acid, glutamic acid, lactic acid, maleic acid, trometamol, and gluconic acid.

3. The pharmaceutical composition according to claim 1, wherein the pharmaceutically acceptable buffer is phosphoric acid.

4. The pharmaceutical composition according to claim 1, wherein the concentration of the pharmaceutically acceptable buffer is 5 to 100 mmol/L.

5. The pharmaceutical composition according to claim 1, wherein the pharmaceutical composition is a liquid preparation.

6. The pharmaceutical composition according to claim 1, wherein the surfactant is one, or two or more selected from the group consisting of polysorbates and poloxamer 188.

7. The pharmaceutical composition according to claim 1, wherein the surfactant is polysorbate 80.

8. The pharmaceutical composition according to claim 1, wherein a content of the surfactant is 0.001 to 1% (w/v).

9. The pharmaceutical composition according to claim 1, wherein the content of the surfactant is 0.01 to 0.2% (w/V).

10. The pharmaceutical composition according to claim 1, wherein when the pharmaceutical composition is stored, each content of a degradant and a multimer is 10% or less, or a content of a chemically modified substance is 50% or less.

11. The pharmaceutical composition according to claim 1, comprising an anti-human TSLP receptor antibody comprising a heavy chain consisting of the amino acid sequence of SEQ ID NO: 1, and a light chain consisting of the amino acid sequence of SEQ ID NO: 3.

12. The pharmaceutical composition according to claim 1, comprising an anti-human TSLP receptor antibody consisting of amino acid sequences of an antibody generated by a post-translational modification of an anti-human TSLP receptor antibody comprising a heavy chain consisting of the amino acid sequence of SEQ ID NO: 1, and a light chain consisting of the amino acid sequence of SEQ ID NO: 3.

13. The pharmaceutical composition according to claim 1, comprising an anti-human TSLP receptor antibody comprising a heavy chain consisting of the amino acid sequence of amino acids 1-447 of SEQ. ID NO: 1, and a light chain consisting of the amino acid sequence of SEQ ID NO: 3.

14. The pharmaceutical composition according to claim 1, comprising an anti-human TSLP receptor antibody comprising a heavy chain consisting of the amino acid sequence SEQ ID NO: 1, and a light chain consisting of the amino acid sequence of SEQ ID NO: 3, and an anti-human TSLP receptor antibody comprising a heavy chain consisting of the amino acid sequence of amino acids 1-447 of SEQ ID NO: 1, and a light chain consisting of the amino acid sequence of SEQ ID NO: 3.

* * * * *

SEQUENCE LISTING

```
<160> NUMBER OF SEQ ID NOS: 4

<210> SEQ ID NO 1
<211> LENGTH: 448
<212> TYPE: PRT
<213> ORGANISM: Artificial Sequence
<220> FEATURE:
<223> OTHER INFORMATION: H-chain of anti-human TSLP Receptor antibody

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Ser
            20                  25                  30

Ala Met His Trp Val Arg Gln Ala Pro Gly Lys Gly Leu Lys Trp Val
        35                  40                  45

Ser Ser Val Ser Gly Ser Gly Ala Gly Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Glu Gly Gly Ser Arg Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 2
<211> LENGTH: 1347
<212> TYPE: DNA
<213> ORGANISM: Artificial Sequence
<220> FEATURE:
<223> OTHER INFORMATION: H-chain gene of anti-human TSLP Receptor
      antibody

<400> SEQUENCE: 2
gaggtgcagc tgttggagtc tgggggaggc ttggtacagc cggggggtc cctgagactc      60 tcctgtgcag cctctggatt cacctttcgc agctctgcca tgcattgggt ccgccaggct    120
ccagggaagg gactgaaatg gtctcaagt gttagtggca gtggtgctgg aacatactac     180
gcagactccg tgaagggccg gttcaccatc tccagagaca atcccaagaa tacactgtat    240
ctgcaaatga acagtctgag agccgaggac acggccgtat attattgtgt gaaagaaggg    300
ggcagccggg gttttgacta ctggggccag ggaaccctgg tcaccgtctc ctcagcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540 tactcccttagtagcgtggt gaccgtgccc tccagcagct tgggcaccca gacctacatc    600
tgcaacgtga atcacaagcc cagcaacacc aaggtggaca gaaagttga gcccaaatct    660

-continued

```
tgtgacaaaa ctcacacatg cccaccgtgc ccagcacctg aactcctggg gggaccgtca    720
gtcttcctct ccccccaaaa cccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaatga                                       1347
```

<210> SEQ ID NO 3
<211> LENGTH: 214
<212> TYPE: PRT
<213> ORGANISM: Artificial Sequence
<220> FEATURE:
<223> OTHER INFORMATION: L-chain of anti-human TSLP Receptor antibody

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Leu Tyr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 4
<211> LENGTH: 645

```
<212> TYPE: DNA
<213> ORGANISM: Artificial Sequence
<220> FEATURE:
<223> OTHER INFORMATION: L-chain gene of anti-human TSLP Receptor
      antibody

<400> SEQUENCE: 4
gacatccaga tgacccagtc tccatcctca ctgtctgcat ctgtaggaga cagagtcacc        60
atcacttgtc gggcgagtca ggacattagc aattatttag cctggtttca gcagaaacca       120
gggaaagccc ctaagtccct gatctatact gcatccagtt tgcaaagtgg ggtcccatca       180
aagttcagcg gcagtggatc tgggacagat ttcactctca ccatcagcag cctgcagcct       240
gaagattttg caacttatta ctgccaacag tataatcttt atcctccgac gttcggccaa       300
gggaccaagg tggaaatcaa acggactgtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag cacccctgacg      540 ctgagcaaag cagactacga gaaacacaaa gtctacgcct gcgaagtcac ccatcagggc       600
ctgagctcgc ccgtcacaaa gagcttcaac aggggagagt gttag                       645
```